(12) United States Patent
Boggs et al.

(10) Patent No.: US 11,541,235 B2
(45) Date of Patent: Jan. 3, 2023

(54) DEVICES AND METHODS FOR DELIVERY OF ELECTRICAL CURRENT FOR PAIN RELIEF

(71) Applicant: SPR THERAPEUTICS, INC., Cleveland, OH (US)

(72) Inventors: Joseph W. Boggs, Chapel Hill, NC (US); Amorn Wongsarnpigoon, Chapel Hill, NC (US); Matthew G. deBock, Morrisville, NC (US); Nathan Crosby, Cleveland, OH (US)

(73) Assignee: SPR THERAPEUTICS, INC., Cleveland, OH (US)

( * ) Notice: Subject to any disclaimer, the term of this patent is extended or adjusted under 35 U.S.C. 154(b) by 165 days.

(21) Appl. No.: 15/688,418

(22) Filed: Aug. 28, 2017

(65) Prior Publication Data
US 2018/0056066 A1 Mar. 1, 2018

Related U.S. Application Data

(60) Provisional application No. 62/380,097, filed on Aug. 26, 2016.

(51) Int. Cl.
*A61N 1/36* (2006.01)
*A61N 1/05* (2006.01)

(52) U.S. Cl.
CPC ..... *A61N 1/36021* (2013.01); *A61N 1/36017* (2013.01); *A61N 1/36071* (2013.01); *A61N 1/0502* (2013.01); *A61N 1/36034* (2017.08)

(58) Field of Classification Search
CPC ............ A61N 1/36021; A61N 1/36017; A61N 1/36071; A61N 1/36034; A61N 1/0502
(Continued)

(56) References Cited

U.S. PATENT DOCUMENTS

| 5,330,515 A | 7/1994 | Rutecki |
| 5,873,900 A | 2/1999 | Maurer |

(Continued)

FOREIGN PATENT DOCUMENTS

| WO | WO2010/014260 | 2/2010 |
| WO | WO2010044880 | 4/2010 |

(Continued)

OTHER PUBLICATIONS

Rauck et al., Treatment of Post-Amputation Pain With Peripheral Nerve Stimulation, Neuromodulation 2014; 17: 188-197 (Year: 2014).*

(Continued)

*Primary Examiner* — Carl H Layno
*Assistant Examiner* — Manolis Pahakis
(74) *Attorney, Agent, or Firm* — McDonald Hopkins LLC

(57) ABSTRACT

Device/system that provides pain relief by delivering stimulation that neither generates action potentials nor completely blocks neural transmission (in the peripheral nerve). The present teachings provide relief by modulating release of neurotransmitters in peripheral nerves to cause neuromodulation at the level of the peripheral nerve (modulation of neural signals in the peripheral nerve). The present teachings provide relief by modulating release of neurotransmitters in peripheral nerves to cause neuromodulation at the level of the peripheral nerve (modulation of neural signals in the peripheral nerve) to alter the frequency of physiologically generated neural transmission.

11 Claims, 13 Drawing Sheets

(58) Field of Classification Search
USPC .......................................................... 607/46
See application file for complete search history.

(56) References Cited

U.S. PATENT DOCUMENTS

| | | | |
|---|---|---|---|
| 6,167,304 A | 12/2000 | Loos | |
| 6,381,496 B1 | 4/2002 | Meadows et al. | |
| 6,530,954 B1 | 3/2003 | Eckmiller | |
| 6,671,544 B2 | 12/2003 | Baudino | |
| 6,735,475 B1 | 5/2004 | Whitehurst | |
| 7,024,247 B2* | 4/2006 | Gliner | A61N 1/36082 607/48 |
| 7,079,882 B1 | 7/2006 | Schmidt | |
| 7,242,983 B2 | 7/2007 | Frei | |
| 7,302,296 B1 | 11/2007 | Hoffer | |
| 7,324,853 B2 | 1/2008 | Ayal | |
| 7,337,005 B2 | 2/2008 | Kim | |
| 7,359,751 B1 | 4/2008 | Erickson et al. | |
| 7,369,894 B2 | 5/2008 | Gerber | |
| 7,373,204 B2 | 5/2008 | Gelfand et al. | |
| 7,613,519 B2 | 11/2009 | De Ridder | |
| 7,725,178 B2* | 5/2010 | Chen | A61N 1/37258 607/118 |
| 7,761,166 B2 | 7/2010 | Giftakis | |
| 7,792,591 B2 | 9/2010 | Rooney | |
| 7,945,330 B2 | 5/2011 | Gilner et al. | |
| 8,380,318 B2* | 2/2013 | Kishawi | A61N 1/36021 607/46 |
| 8,788,046 B2 | 7/2014 | Bennett | |
| 8,788,047 B2 | 7/2014 | Bennett | |
| 8,788,048 B2 | 7/2014 | Bennett | |
| 8,855,776 B2* | 10/2014 | Lin | A61N 1/36171 607/45 |
| 9,381,360 B2* | 7/2016 | Hershey | A61N 1/37247 |
| 9,427,574 B2* | 8/2016 | Lee | A61N 1/0558 |
| 9,925,381 B2* | 3/2018 | Nassif | A61N 1/3787 |
| 2001/0018606 A1 | 8/2001 | Ingle | |
| 2002/0099419 A1 | 7/2002 | Cohen | |
| 2003/0100933 A1 | 5/2003 | Ayal | |
| 2003/0114886 A1* | 6/2003 | Gluckman | A61N 1/36031 607/2 |
| 2004/0015204 A1 | 1/2004 | Whitehurst et al. | |
| 2004/0158298 A1* | 8/2004 | Gliner | A61N 1/36021 607/48 |
| 2004/0186532 A1 | 9/2004 | Tadlock | |
| 2005/0143789 A1 | 6/2005 | Whitehurst | |
| 2005/0149154 A1 | 7/2005 | Cohen | |
| 2005/0182469 A1 | 8/2005 | Hunter | |
| 2005/0192644 A1* | 9/2005 | Boveja | A61N 1/36014 607/45 |
| 2005/0246006 A1 | 11/2005 | Daniels | |
| 2006/0052856 A1* | 3/2006 | Kim | A61N 1/36071 607/117 |
| 2006/0069415 A1 | 3/2006 | Cameron et al. | |
| 2006/0095088 A1 | 5/2006 | De Ridder | |
| 2006/0173507 A1 | 8/2006 | Mrva et al. | |
| 2006/0195170 A1 | 8/2006 | Cohen | |
| 2006/0206166 A1 | 9/2006 | Weiner | |
| 2007/0021803 A1 | 1/2007 | Deem et al. | |
| 2007/0027514 A1 | 2/2007 | Gerber | |
| 2007/0150034 A1 | 6/2007 | Rooney et al. | |
| 2007/0244522 A1 | 10/2007 | Overstreet | |
| 2008/0132982 A1 | 6/2008 | Gerber | |
| 2008/0294226 A1* | 11/2008 | Moffitt | A61N 1/36167 607/74 |
| 2009/0192567 A1 | 7/2009 | Armstrong | |
| 2009/0281594 A1 | 11/2009 | King | |
| 2009/0326613 A1 | 12/2009 | Knoblich | |
| 2010/0030300 A1 | 2/2010 | Feler | |
| 2010/0036280 A1 | 2/2010 | Ballegaard | |
| 2010/0036454 A1* | 2/2010 | Bennett | A61N 1/36021 607/46 |
| 2010/0125313 A1* | 5/2010 | Lee | A61N 1/36071 607/46 |
| 2010/0152808 A1 | 6/2010 | Boggs | |
| 2010/0152809 A1 | 6/2010 | Boggs, II | |
| 2010/0198298 A1* | 8/2010 | Glukhovsky | A61N 1/36021 607/46 |
| 2010/0280576 A1 | 11/2010 | Gerber | |
| 2011/0022114 A1 | 1/2011 | Navarro | |
| 2011/0054565 A1 | 3/2011 | Wacnik | |
| 2011/0098777 A1* | 4/2011 | Silverstone | A61N 1/36025 607/45 |
| 2011/0106207 A1 | 5/2011 | Cauller | |
| 2011/0276107 A1* | 11/2011 | Simon | A61N 2/02 607/46 |
| 2012/0109241 A1* | 5/2012 | Rauscher | A61N 1/326 607/45 |
| 2012/0221075 A1* | 8/2012 | Bentwich | G16H 50/30 607/45 |
| 2012/0290055 A1 | 11/2012 | Boggs | |
| 2012/0310314 A1* | 12/2012 | Bennett | A61N 1/36071 607/115 |
| 2012/0330218 A1* | 12/2012 | Bradley | A61N 1/3605 604/20 |
| 2013/0238066 A1* | 9/2013 | Boggs, II | A61N 1/0502 607/116 |
| 2013/0338743 A1* | 12/2013 | Starobin | A61N 1/0456 607/115 |
| 2014/0330335 A1* | 11/2014 | Errico | A61B 5/4064 607/45 |
| 2014/0364920 A1* | 12/2014 | Doan | A61N 1/37247 607/46 |
| 2015/0174397 A1* | 6/2015 | Bhadra | A61N 1/36071 607/117 |
| 2015/0209587 A1* | 7/2015 | Lee | A61N 1/0551 607/46 |
| 2016/0045751 A1* | 2/2016 | Jiang | A61N 1/36135 607/59 |
| 2016/0082269 A1 | 3/2016 | Moffitt | |
| 2016/0256689 A1* | 9/2016 | Vallejo | A61N 1/36192 |
| 2018/0056066 A1* | 3/2018 | Boggs | A61N 1/36071 |

FOREIGN PATENT DOCUMENTS

| | | |
|---|---|---|
| WO | WO2012/075497 | 6/2012 |
| WO | WO2013036630 | 3/2013 |
| WO | WO2014/099423 | 6/2014 |

OTHER PUBLICATIONS

Matsuo et al., Early transcutaneous electrical nerve stimulation reduces hyperalgesia and decreases activation of spinal glial cells in mice with neuropathic pain, Pain 155 (2014) 1888-1901 (Year: 2014).*

Plazier et al., C2 Nerve Field Stimulation for the Treatment of Fibromyalgia: A Prospective, Double-blind, Randomized, Controlled Cross-over Study, Brain Stimulation 8 (2015) 751-757 (Year: 2015).*

International Preliminary Report on Patentability, NDI Medical, LLC, PCT/US2009/06414, dated Jan. 7, 2011.

International Search Report and the Written Opinion of the International Searching Authority, NDI Medical, LLC, PCT/US2009/06403, dated Feb. 23, 2010.

International Search Report and the Written Opinion of the International Searching Authority, PCT/US2013/73647, SPR Therapeutics, LLC, dated Feb. 20, 2014.

International Search Report and the Written Opinion of the International Searching Authority, PCT/US2012/53952, SPR Therapeutics, LLC, dated Nov. 15, 2012.

Extended European Search Report for Application EP13866258.0 PCT/US2013073647, dated Sep. 5, 2016, European Patent Office, Germany.

International Search Report and Written Opinion dated Mar. 15, 2012 in International Patent Application Serial No. PCT/US11/62882.

International Search Report and Written Opinion dated Mar. 9, 2012 in International Patent Application Serial No. PCT/US2011/062857.

(56) References Cited

OTHER PUBLICATIONS

International Preliminary Report on Patentability dated Dec. 6, 2012 from PCT application PCT/US11/62906 filed Dec. 1, 2011.
International Search Report and Written Opinion dated Mar. 30, 2012 in International Patent Application Serial No. PCT/US2011/062906.
International Search Report and Written Opinion dated Oct. 27, 2017 in International Patent Application Serial No. PCT/US2017/048904.

* cited by examiner

DEVICES AND METHODS FOR DELIVERY OF ELECTRICAL CURRENT FOR PAIN RELIEF

RELATED APPLICATIONS

This application claims priority to and incorporates by reference U.S. Provisional Patent Application No. 62/380,097, filed on Aug. 26, 2016.

FIELD OF INVENTION

The present disclosure generally relates to a device/system that provides pain relief by delivering electrical current that neither generates action potentials nor completely blocks neural transmission (in the peripheral nerve), i.e., subthreshold pain relief system and method.

BACKGROUND

It is generally recognized that the perception of pain, especially non-acute pain such as sub-acute or chronic pain, in mammals can be caused, worsened, and/or sustained in duration by a sensitization (e.g., hyperexcitability, or increased propensity or likelihood of activation) of afferent sensory receptors and/or the central nervous system fibers that receive direct and/or indirect signals from the afferent sensory receptors, including free nerve endings, to noxious or conventional or previously non-noxious stimuli. Sensitization is the process whereby previously non-noxious stimuli are perceived as painful, and this is an integral part of the development and maintenance of chronic pain (as opposed to the acute, healthy pain response). Such sensitization may result from non-nociceptive primary afferents (e.g. A.beta.) sprouting to make inappropriate and/or additional connections in the spinal cord, from the loss of inhibition in the central nervous system (e.g. spinal cord, and/or brain), and/or from plasticity resulting from changes in functional connectivity.

SUMMARY OF INVENTION

Specific reference is made to the appended claims, drawings, and description below, all of which disclose elements of the invention. While specific embodiments are identified, it will be understood that elements from one described aspect may be combined with those from a separately identified aspect. In the same manner, a person of ordinary skill will have the requisite understanding of common processes, components, and methods, and this description is intended to encompass and disclose such common aspects even if they are not expressly identified herein.

In one aspect, the invention may include any combination of the following features:
  delivering electric current altering transmission and/or production of action potentials in nerve tissue including a nerve cell body, dendrites, axons, axon hillocks, and/or other nerve fibers without directly stimulating an action potential in a nerve;
  wherein the electric current causes at least one of: (a) changes to a frequency of one or more action potentials; (b) changes in probability of one or more action potentials occurring; (c) changes in excitability of at least one nerve; (d) changes to conduction velocity, shape, form, features, interpulse interval, period, rate, coefficient of variation, or duration of one or more action potentials and (e) changes to timing, spacing, or pattern of one or more action potentials or trains of action potentials;
  wherein the electrical current does not cause a perception of paresthesias;
  wherein the electrical current does not block or interrupt efferent signals and motor nerve signals;
  wherein the electrical current alters action potentials in the neural targets via activation, inactivation, excitation, or suppression of non-neural tissue;
  wherein the non-neural tissue is a glial cell;
  wherein the electrical current is delivered through an electrode located 1.0 mm or more away from the nerve body;
  altering transmission of action potentials in one of a nerve cell body (or soma), dendrites, axons, axon hillocks, and/or other nerve fibers by: (a) changing a probability of one or more action potentials occurring; (b) changing excitability of at least one nerve; and/or (c) changing conduction velocity, shape, form, features, interpulse interval, period, rate, coefficient of variation, or duration of one or more action potentials;
  wherein the features are at least one selected from depolarization, overshoot, peak, repolarization, hyperpolarization, and refractory period; and
  delivering electrical current to a peripheral nerve to relieve pain while avoiding generation of paresthesia in the distribution of the nerve and while avoiding blocking the nerve such that the delivery of electrical current is imperceptible to the patient except for the reduction of the perception of pain.

In another aspect, the invention may include a system having any combination of the following features:
  a percutaneous electrode;
  an electrical pulse generator delivering electrical current to at least a portion of a peripheral nervous system, through the electrode, in a manner that causes a reduction of perception of pain while avoiding generation of action potentials in a targeted nerve fiber;
  wherein the electrical current avoids a perception of paresthesia;
  wherein the electrical current avoids generating one or more action potentials in a sensory nerve fiber that would cause a perception of pain;
  wherein the electrical current avoids generating action potentials in an efferent nerve fiber that would cause or block a muscle contraction;
  wherein the electrical current avoids a perception of numbness or tingling;
  an electrode percutaneously inserted in-vivo,
  an electrical pulse generator applying electrical current to at least a portion of a peripheral nervous system through the electrode in a manner that causes a reduction of perception of pain while avoiding generating action potentials in a sensory nerve fiber that would cause a perception of paresthesia, while avoiding generating one or more action potentials in a sensory nerve fiber that would cause a perception of pain, while avoiding generating action potentials in an efferent nerve fiber that would cause or block a muscle contraction, and while avoiding block of comfortable sensations, avoiding a perception of numbness or tingling; and
  an electrical pulse generator applying electrical current to at least a portion of a peripheral nervous system through the electrode in a manner that causes a reduction of perception of pain while avoiding generating action potentials in a type Ia or Ib sensory nerve fiber that would cause a perception of paresthesia, while avoiding generating one or more action potentials in a type III or IV sensory nerve fiber that would cause a perception of pain, while avoiding generating action potentials in an efferent nerve fiber that would cause or block a muscle contraction, while avoiding block of comfortable sensations, and avoiding complete block of type III or type IV sensory fibers enabling the perception of pain that corresponds to tissue damage.

BRIEF DESCRIPTION OF THE DRAWINGS

Operation of the disclosure may be better understood by reference to the following detailed description taken in connection with the following illustrations. Any numbers or printed indicia on the drawings are hereby incorporated within this written disclosure.

DETAILED DESCRIPTION OF CERTAIN ASPECTS OF THE INVENTION

Figure 1A:
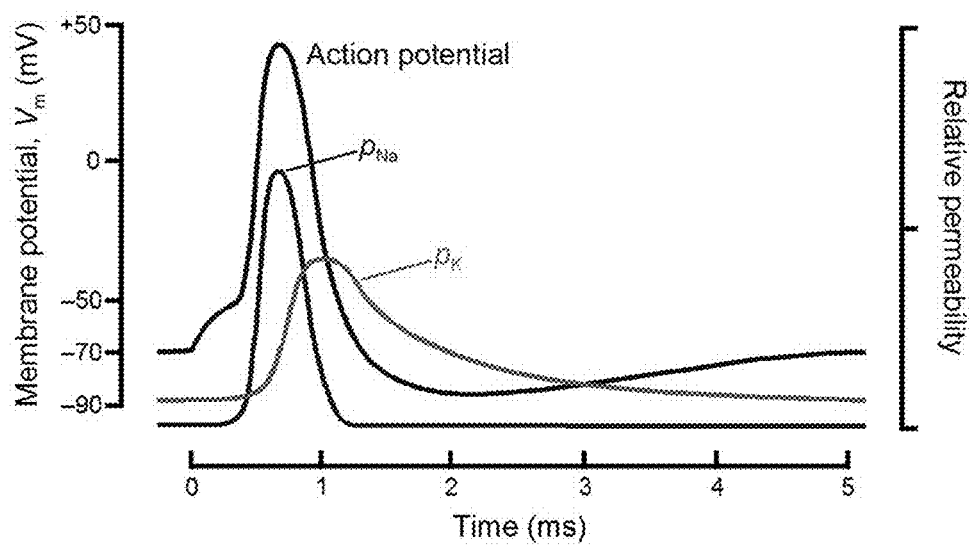
FIGS. 1A and 1B are graphs showing the ion permeability and conductances, respectively speaking, of the neural membrane, both of which may be modulated by electrical signals according to certain aspects of the invention.

Reference will now be made in detail to exemplary embodiments of the present invention, examples of which are illustrated in the accompanying drawings. It is to be understood that other embodiments may be utilized and structural and functional changes may be made without departing from the respective scope of the invention. As such, the following description is presented by way of illustration only and should not limit in any way the various alternatives and modifications that may be made to the illustrated embodiments and still be within the spirit and scope of the invention.

As used herein, the words "example" and "exemplary" mean an instance, or illustration. The words "example" or "exemplary" do not indicate a key or preferred aspect or embodiment. The word "or" is intended to be inclusive rather an exclusive, unless context suggests otherwise. As an example, the phrase "A employs B or C," includes any inclusive permutation (e.g., A employs B; A employs C; or A employs both B and C). As another matter, the articles "a" and "an" are generally intended to mean "one or more" unless context suggest otherwise.

Any elements described herein as singular can be pluralized (i.e., anything described as "one" can be more than one). Any species element of a genus element can have the characteristics or elements of any other species element of that genus. The described configurations, elements or complete assemblies and methods and their elements for carrying out the invention, and variations of aspects of the invention can be combined and modified with each other in any combination.

Embodiments of the present invention include improved systems and methods of pain reduction by delivering electrical current that neither generates action potentials nor completely blocks neural transmission in a peripheral nerve. Delivery of electrical current without generation of an action potential could also, for the purposes of the described invention, include generation of an imperceptible neural signal, for example a limited number of action potentials generated within a sufficiently long time so as to not be perceived, but which might be perceived if they were generated at a sufficiently high rate. Alternatively, for the purposes of the described invention, stimulation without generation of an action potential could refer to generation of a perceptible neural signal that replicates normal or typically experienced sensations, including but not limited to touch, stretching, or other sensations.

The delivery of electrical current for purposes of this invention is and must be distinguished from the delivery of electrical stimulation, which is known in this field. That is, an electrical current that evokes an action potential is electrical stimulation. Numerous publications disclose such stimulation regimes where, upon establishing the threshold for action potentials, and the characteristics of the current are further manipulated to generate and/or sustain specific types of action potentials above that threshold. In contrast, certain embodiments of this invention rely on identifying the action potential threshold and then creating and delivering electrical current patterns that do not exceed the threshold (i.e., they remain "subthreshold," so that the patient does not perceive any tingling, action potentials, or other definitive sensations).

Further, electrical current and/or creating an electrical field potential or voltage may include exciting and/or inhibiting (and in some cases both) cellular activity. More broadly, electrical current and/or signals will alter the electrical field, the electrical potential, and/or gradient such that cellular activity is and/or can be modified to reduce the perception of pain during and/or after the delivery of the electrical current and/or electrical signal and/or the change in electrical potential and/or voltage caused by the device.

Generally speaking, the delivery of current, the creation of electrical fields, and in some cases stimulation under this invention serves two main goals: subthreshold stimulation for pain relief (in which no action potentials are sustained, thereby focusing only on current) and sub-perception stimulation for pain relief (action potentials are created but don't result in perception of stimulation).

For the purposes of this invention, pain may refer to chronic, acute, post-surgical, neuropathic, musculoskeletal, and/or other types or sources of pain. Additional embodiments include inventive systems, methods, and instructions for use of the systems and/or methods of pain reduction and/or relief by delivering stimulation that generates action potentials in such a way that stimulation is not perceived, minimally perceived, and/or comfortably perceived by the subject receiving stimulation, and which avoids completely blocking, partially blocking, and/or blocking neural transmission in a peripheral nerve or nerves.

The invention reduces pain during and/or after the delivery of electrical signals, current, or stimulation while also maintaining the other functions of the nerve (both during and after the delivery of electrical current or stimulation so as to avoid interrupting, impeding, and/or blocking ascending or descending, including orthodromic or antidromic, action potentials or neural signals that are healthy, normal, functional, and/or otherwise desirable to preserve, maintain, facilitate, and/or enable). The invention also avoids generating unwanted responses, sensations, and/or effects such as unwanted muscle movements during and/or after the delivery of electrical current or stimulation (e.g., without and/or while avoiding generating unwanted sensations, paresthesias, discomfort, pain and/or muscle contractions) while enabling desired nerve functions to continue without alteration or inhibition (e.g., providing pain relief while facilitating and/or enabling the generation and/or transmission of action potentials or neural signals that are healthy, normal, functional, and/or otherwise desirable and/or unrelated to pain).

In one aspect, the invention may enable reduction of pain while avoiding changing nerve functions that do no relate to pain. In this manner, the effects of the invention can be made specific and desirably limited to pain and pain reduction to avoid affecting non-pain related nerve functions and to avoid causing unwanted sensations or other unwanted nerve functions.

One method according to the present invention is a novel use of electrical signals, current, or stimulation with a device to relieve, reduce, and/or alter pain and/or the perception of pain by altering the transmission of action potentials in a peripheral nerve fiber during delivery of electrical signals, current, or stimulation and/or after the delivery of electrical signals, current, or stimulation (e.g., while the device is "on" and/or after the device is "off" once electrical signals, current, or stimulation have been delivered and then stopped). Altering the transmission of action potentials may occur in the nerve cell body (or soma), dendrites, axons, axon hillocks, and/or other structures and components of nerve fibers and may include, as non-limiting examples:

changing the instantaneous, effective, average, or overall frequency of one or more action potentials; changing the timing, spacing, or pattern of one or more action potentials or trains of action potentials; and/or changing the probability of one or more action potentials occurring and/or the excitability of one or more nerves; and/or changing the conduction velocity, shape, form, features (e.g., depolarization, overshoot, peak, repolarization, hyperpolarization, or refractory period), interpulse interval, period, rate, coefficient of variation, or duration of one or more action potentials.

In some aspects, the invention alters transmission to cause changes in the temporal or spatial summation of action potentials in pain processing centers in the peripheral or central nervous system, ultimately decreasing the perception or sensation of pain. Certain neural signals or patterns of action potentials may be interpreted or processed by the spinal cord and/or brain as painful signals (e.g., a threshold frequency or unique firing pattern). Changing the quality of those signals or patterns may alter or prevent the interpretation of those signals as sensations or perceptions of pain. Thus, the inventive systems, devices, and methods deliver electrical signals, current, and/or stimulation to alter the transmission of one or more action potentials, reduce the frequency and/or change the firing pattern of one or more nerves such that the body and the central nervous system no longer recognizes the input or signal from the peripheral nerve or nerves as painful, or may perceive the signal as less painful.

As a non-limiting example, systems, devices, methods, and instructions for use of systems, devices, methods for influencing peripheral nerve activity, signaling, and/or transmission the have been invented and developed that can be deployed outside of the central nervous system to deliver electrical signals, current, and/or stimulation to alter the transmission of one or more action potentials, reduce the frequency and/or change the firing pattern of one or more peripheral nerves such that the body and the central nervous system no longer recognizes the input or signal from the peripheral nerve or nerves as painful, or may perceive the signal as less painful, and the reduction of the perception of pain may be achieved during and sustained after the electrical signals, current, and/or stimulation, such that pain may be eliminated or reduced both while the device is active and the elimination or reduction of pain may or will continue to persist after the device has been deactivated. This invention enables the use of devices, systems, methods, and instructions for use that can produce long-lasting effects and that are desirably minimally invasive and less invasive than existing devices, systems, methods, and instructions, enabling them to be deployed by a larger range of physicians and clinicians to a broader range of patients with pain. This invention enables the use of temporary devices, systems, methods, and instructions for use that can produce long-lasting effects after the devices and systems are deactivated and removed enabling them to be deployed sooner in the treatment continuum by a larger range of physicians and clinicians to a broader range of patients with pain reducing barriers to use. This invention also enables the use of long term and/or permanent devices and systems that are more efficient and/or smaller in profile, surface area, and/or volume. This invention may also enable the use of the devices, systems, and methods, instructions for use of those devices, systems, and methods in patients who will benefit from pain relief and will also benefit from avoiding the generation of unwanted sensations, paresthesias, and/or muscle contractions that typically accompany existing systems, devices, methods, and instructions for peripheral nerve stimulation.

In one embodiment of the present invention, delivery of electrical signals and/or current provides pain relief by altering transmission of action potentials by modulating concentrations of one or more ions (e.g., sodium, potassium, calcium, and/or other ions) around or near a peripheral nerve or nerves. This delivery of electrical signals/currentcauses neuromodulation (i.e. altering transmission of action potentials) at the level of the peripheral nerve. In particular, applying electrical signals/current in the region around a peripheral nerve generates an electrical field that has an effect on concentrations or concentration gradients of charged particles, including ions. Changing and/or moving concentrations of ions in the region around a peripheral nerve may then alter the frequency of physiologically generated neural transmissions, thereby changing the processing or interpretation of the transmission and decreasing the perception of pain. In turn, these changes in concentrations of ions around the outside of a peripheral nerve may cause a shift in the resting membrane potential and/or the voltage across the membrane of the neural structure, ultimately changing the propensity of the neural structure to be activated (i.e. fire one or more action potentials) or to transmit an action potential along a nerve fiber after it was initiated at a different location.

In another embodiment, the invention can cause changes in concentrations of ions around the outside of a peripheral nerve that may cause a shift in the resting membrane potential and/or the voltage across the membrane of the neural structure, ultimately changing the propensity of the neural structure to be de-activated (i.e. to avoid firing one or more action potentials) or to resist, delay, inhibit or otherwise change key properties of the transmission of an action potential (e.g., such as its timing, amplitude, shape, conduction velocity, and/or speed) along a nerve fiber after it was initiated at a different location. It is to be appreciated that these changes may alter transmission of a neural signal without blocking it (e.g., while avoiding blocking it partially and/or completely), and these changes may reduce the perception of pain during and/or after the application of electrical signals/current and/or, in some embodiments, stimulation.

Additionally or alternatively, altering the ion concentration around an axon or other neural structure may increase or decrease the transmembrane potential while action potentials are being transmitted along the target nerve (e.g., from a pain signal, a noxious stimulus, and/or a pain source), such that the change in ion concentration interrupts the action potential. Here, electrical stimulation may affect the transmembrane potential of dendrites and disrupt the summation of post-synpatic potentials, and thus, the transmission of pain signals towards or within the central nervous system. Also, changes in ion concentrations around a peripheral nerve fiber may alter membrane potentials and make certain voltage-gated ion channels more or less likely to open. That is, selective or non-selective channels allowing passage of ions into or out of the cell membrane based on the membrane potential or voltage across the cell membrane can be controlled. Changes in ion channel properties, independently or coupled with changes in availability of ions outside the nerve fiber flowing into the neural structure through the cell membrane, may alter the shape, duration, timing, conduction velocity, or other features of an action potential transmitted through that nerve fiber.

These changes caused directly and/or indirectly by the invention, which may be deployed in the periphery outside of the central nervous system, may desirably alter how the signal is perceived and interpreted by the central nervous system and reduce pain. The invention is designed to cause these changes in perception and/or interpretation of the signal and therefore the reduction and/or elimination of pain to persist and be sustained during and after the use of the invention, such that the invention causes changes that desirably outlast the duration of use of the invention, enabling a short-term temporary device and/or system to produce long-lasting and/or permanent effects, providing sustained pain relief.

As another non-limiting example, changes in ion concentrations and/or ion channel properties as a result of changes in membrane potential may alter refractory periods following transmission of an action potential through a nerve fiber. The amount of time required for ion channels and ion concentrations to recover to a nominal baseline level—and for the neural structure to be ready to fire another action potential following the conduction of an action potential through the neural structure—may be lengthened or shortened by the effects of electrical stimulation and the delivery of electrical current and/or electrical signals, changing the timing or frequency of action potentials being transmitted and decreasing the perception of pain, and/or causing one or more action potentials to fail to fire, thus disrupting the neural signal.

The invention may be designed to be deployed in the periphery outside of the central nervous system to affect peripheral nerves and/or peripheral neural structures, cells, and/or peripheral support structures, cells, and/or functions to desirably disrupt the neural signal(s) in peripheral nerves. The invention may desirably cause disruption of neural signaling within peripheral nerves in a way that desirably cause disruption in neural signaling within the central nervous system such that pain is eliminated or reduced while avoiding the need for the device to be placed in, on, or near the central nervous system and while avoiding disruption of desirable nervous function within the peripheral nervous system and/or the central nervous system. Thus, the system(s) and device(s) may be deployed outside of the central nervous system to directly and/or indirectly affect peripheral nerve activity to directly and/or indirectly affect central nervous system activity to eliminate or reduce the perception of pain. The invention enables changes to be caused within the central nervous system without the risk of placing a device in, on, or near the central nervous system or surrounding or nearby space (e.g., without placing a device in, on, or near the epidural space) and reduces risk to the patient (e.g., by avoiding risks associated with spinal cord stimulation (SCS) and/or dorsal root ganglion (DRG) stimulation) while providing clinically meaningful benefits of pain relief that can be sustained long term.

Figure 1B:
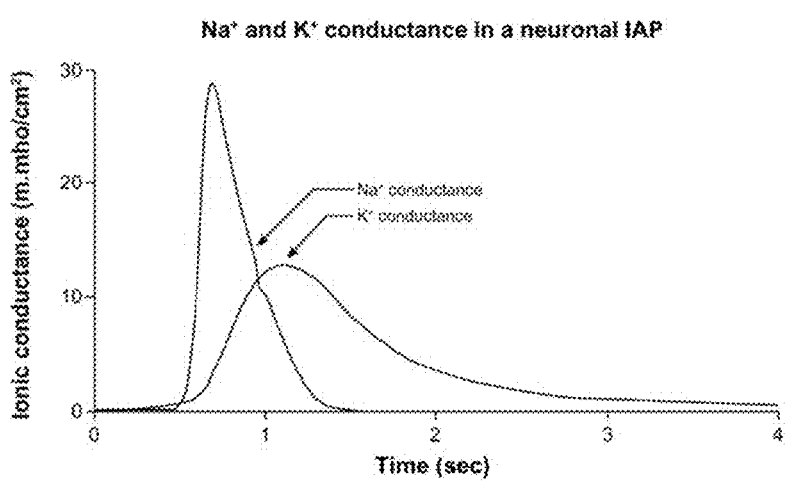

As another non-limiting example, electrical stimulation may substantially decrease or deplete the supply of one or more ions within a given area around a neural structure such as an axon, and as a result, the stimulation waveform and/or pulse train being transmitted along the neural structure is changed. FIGS. 1A and 1B show how membrane permeability and conductance are can be impacted relative to one another. These changes may include, but are not limited to, inability of an axon to propagate an action potential because insufficient ions are available to flow through the ion channels in the axonal membrane; changes in action potential shape due to decreased supply of specific ions, potentially causing an imbalance among ions; and increases in firing rate due to changes in depolarization, hyperpolarization, and/or repolarization during an action potential.

The aforementioned ways in which electrical stimulation may decrease pain perception by modulating concentrations of ions around the outside of a peripheral nerve fiber also can be effectuated by modulating concentrations of ions and/or other charged particles (e.g., sodium, potassium, calcium, and/or other ions) inside peripheral nerves. This modulating concentration causes a corresponding neuromodulation (e.g., altering transmission of action potentials) at the level of the peripheral nerve.

In another aspect of the present invention, delivery of electrical stimulation or, more preferably current and/or electrical signals or signaling provides pain relief by altering transmission of action potentials via modulation of neurotransmitter release. Neurotransmitter release is increased or decreased at synapses between neurons (e.g., between neurons in sensory pathways that transmit painful and/or non-painful sensory information from the periphery) and/or at synapses between neurons and other structures, such as neuromuscular synapses. As non-limiting examples, the changes that are caused directly or indirectly by the invention in synapses (e.g., the synaptic function and/or transmission) may occur in the periphery, such as axo-axonic synapses between axons in a peripheral nerve, or in the central nervous system (CNS), such as the central terminals of sensory fibers that synapse in the spinal cord. In a non-limiting example, the invention may cause changes in synaptic function, synaptic transmission, transmitter release, binding, and/or uptake (and/or re-uptake) to reduce the perception of pain following and/or during the delivery of electrical stimulation, current, and/or electrical signals or signaling to produce sustained reductions in pain through alteration of transmission of neural signals via modulation of neurotransmitter release.

Further as a non-limiting example, the present method, systems, devices, and instructions for use of electrical stimulation and/or delivery of electrical current and/or signals may alter the release, binding, and/or reuptake of excitatory neurotransmitters at a synapse. In turn, this release, binding, and/or reuptake alters the temporal and/or spatial summation of excitatory postsynaptic potentials and changing the timing, frequency, or pattern of one or more action potentials crossing the synapse and changing the nature or interpretation of the one or more action potentials to decrease the perception of pain.

Still further, the present method of electrical stimulation may alter the release of inhibitory neurotransmitters. Neurotransmitters may include, as non-limiting examples, amino acids (e.g., glutamate, aspartate, D-serine, GABA, glycine), gasotransmitters (e.g., nitric oxide, carbon monoxide, hydrogen sulfide), monoamines (e.g., dopamine, norepinephrine, epinephrine, histamine, serotonin), peptides or neuropeptides (e.g., somatostatin, substance P, cocaine, endogenous opioids), purines (e.g., ATP, adenosine), or acetylcholine.

According to another aspect of the present invention, electrical stimulation provides pain relief by altering transmission of action potentials through the modulation of release, kinetics (e.g., receptor binding, agonism, antagonism, or reuptake), and/or dynamics (e.g., mobility or concentration gradients) of endogenous neuromodulatory substances. Some endogenous neuromodulatory substances may also act as neurotransmitters (as described above), but have other roles in modulating neuronal function aside from transmitting neural signals across synapses. Neuromodulatory substances may include, as examples, endogenous opioids (e.g., endorphins, enkephalins, dynorphins, endomorphins), enzymes, growth factors, amino acids, neurotransmitters outside of their role in transmitting action potentials across synapses, and peptides and neuropeptides (e.g., somatostatin, oxytocin, substance P, neuropeptide Y). Electrical stimulation may increase the release of neuromodulatory substances and, more particularly, those that have an inhibitory effect of neurotransmission.

As a non-limiting example, stimulation in the region of a peripheral nerve (e.g., within 1-30 mm, 0.1-50 mm, and/or 0.01-100 mm) may induce the release of endogenous opioids that bind to opioid receptors on neural structures and inhibit, slow, or modulate transmission of neural signals and/or dis-sensitize Type III and Type IV fibers that transmit pain signals. Electrical stimulation may decrease the release of neuromodulatory substances that have an excitatory effect on neurotransmission. As a non-limiting example, stimulation in the region of a peripheral nerve may reduce levels or release of substance P, a neuropeptide known to amplify or excite cellular processes and, in particular, sensitize nerve fibers that transmit pain signals.

Many neurotransmitters and neuromodulatory substances are charged particles, or molecules that have residual positive or negative electrical charge based on their molecular structure. The present method of electrical stimulation may exert direct effects on charged particles, altering their concentration, concentration gradients, or mobility in the induced electrical field around or in the region of a peripheral nerve. The method of electrical stimulation described herein may also alter the transmission of action potentials by increasing or decreasing concentrations of neurotransmitters or neuromodulatory substances around a peripheral nerve. As a non-limiting example, electrical stimulation in the region around a peripheral nerve may alter concentrations and/or mobility of adenosine triphosphate (ATP), which is a molecule with a residual negative charge that acts as a neurotransmitter at synapses between neurons in sensory pathways in the peripheral and central nervous systems. Changing the ability of ATP to cross a synapse and bind to its receptor on the postsynaptic cell may change the reliability of synaptic transmission, or alter the timing, shape, frequency, or pattern of one or more action potentials that are being transmitted through the neural structures and across the synapses within, adjacent to, or outside the electrical field. It is to be appreciated that the invention can cause these types of changes to occur to reduce pain without and/or while avoiding generating unwanted responses in the periphery or the central nervous system such as unwanted sensations, unwanted paresthesias, and/or unwanted muscle contractions.

As a non-limiting example, it is to be appreciated that sensations, paresthesias, and/or muscle contractions, based upon action potential thresholds, could be generated selectively or unselectively by the invention in a way that is designed to not detract from the reduction or elimination of pain.

In one embodiment, the present method, device, system, and instructions utilize electrical stimulation to decrease the sensation or perception of pain by decreasing activity (without completely blocking transmission) in Type III and Type IV fibers that transmit pain signals. Type III and Type IV fibers are associated with free nerve endings, touch and pressure receptors, nociceptors, and other nerve endings and receptors that are competent to sense and signal painful stimuli. Thus, by decreasing activity in Type III and Type IV fibers, the tone or activity upstream in neural structures that receive, process, and transmit pain in the CNS are decreased, enabling decreased sensation and/or perception of pain.

In another embodiment of the present invention, electrical current/signaling are used to decrease the sensation or perception of pain by decreasing activity in Type I/II fibers that have become sensitized (or hyperexcitable, or more likely to be activated in response to a sensory stimulus) and/or non-nociceptive primary afferents that signal painful sensations because of sensitization. As a non-limiting example, the present method utilizes electrical signaling, current, and/or stimulation to slow, inhibit, and/or change the shape of action potentials to reduce the temporal or spatial summation of action potentials at synapses between neural elements in pain pathways, resulting in a decrease in the net activation of those pathways and a decrease in the sensation or perception of pain. Decreases in activity could also change the instantaneous, average, or effective frequency, timing, or pattern of one or more action potentials in a way that changes the interpretation of the signal to be less intense or less painful, or make the signal less recognizable as a painful signal (e.g., such that the neural signal is not perceived in a way that generates pain).

In another aspect of the present method, electrical signaling/current decreases the sensation and/or perception of pain by increasing activity (without directly inducing action potentials) in Type III and/or Type IV fibers or by changing the instantaneous, average, or effective frequency, timing, or pattern of one or more action potentials in a way that changes the interpretation of the signal to be less intense or less painful. Some sensations are produced by certain patterns or frequencies of action potentials transmitted through sensory fibers, and retuning or altering the average frequency of action potentials changes the perception of a signal to be less painful. Additionally or separately, changing the timing and pattern of one or more action potentials also changes the perception of a signal to be less painful, for example, by decreasing the regularity and increasing the randomness of a train or sequence of action potentials the signal may be interpreted as non-painful or less painful than a regular, periodic sequence of action potentials.

In another embodiment of the present invention, electrical signaling/current decreases the sensation or perception of pain by increasing activity (without directly inducing action potentials) in Type I and/or Type II fibers. The gate control theory of pain postulates that activity in non-nociceptive afferent fibers, such as the Type I and Type II fibers that typically convey non-painful sensory information, can inhibit the transmission of painful signals from the periphery in response to noxious, painful stimuli, or in the setting of chronic pain when noxious stimuli may no longer be directly applied but painful sensations or perceptions are still felt. Activity in non-nociceptive fibers may therefore be said to "close the gate" on painful signals that are being transmitted from the periphery to the brain. Electrical stimulation in the current method changes the instantaneous, average, or effective frequency, timing, or pattern of one or more action potentials in a way that changes the interpretation of the signal to more effectively "close the gate" or inhibit transmission of pain signals. Changing the timing and pattern of one or more action potentials may also change the perception of a signal, for example, by decreasing the randomness and increasing the regularity of a train or sequence of action potentials in a Type I/II fiber the signal may be interpreted as or become recognizable as non-painful and/or more effectively inhibit transmission of pain signals. Whereas other methods of electrical stimulation in the PNS or CNS directly evoke action potentials, or directly activate neurons, this embodiment of the present method decreases the sensation or perception of pain without causing new action potentials to be transmitted.

Another method according to the present invention includes electrical signaling, current, and/or stimulation to modulate the control of extracellular ions and neurotransmitters by non-neuronal cells while avoiding activation of neuronal cells, enabling the reduction (or prevention) of pain while enabling the avoidance of unwanted sensations (such as paresthesias) and/or the avoidance of unwanted muscle activation (such as muscle contraction). This can be enabled or performed by a device that controls the level of polarization (or depolarization) of one or more non-neuronal cells, such as glial cells, and/or muscle, fat, connective tissue, dermal, and other types of non-neuronal supporting cells, to modulate the extracellular or intracellular levels or concentrations of ion(s) and/or neurotransmitter(s) to inhibit or promote/enhance transmission of neural signals at one or more locations along a neuron. As a non-limiting example, electrical stimulation may alter the concentrations of one or more ion(s), neurotransmitter(s), or other neuromodulatory substance(s) inside or outside of the cell membrane of a non-neuronal supporting cell in the region of a peripheral nerve fiber such that the transmission of action potentials in the nerve fiber is altered in a way that decreases the sensation or perception of pain.

Here, electrical signaling, current, and/or stimulation in the region around or remote to the neural structure modulates the release, concentration, binding, or activity of ion(s), neurotransmitters, and neuromodulators by glial cells that alter the transmission of action potentials in the nerve fiber. Glial cells exist in close proximity to (or in contact with) neural tissues, including cell bodies, soma, axons, synapses, and other neural structures. Glial cells, such as astrocytes, microglia, satellite glial cells, myelinating or non-myelinating Schwann cells, and oligodendrocytes, exert control over the ionic and molecular microenvironment surrounding a neural structure in peripheral nerve, ganglia (e.g., sensory, sympathetic, or parasympathetic), or the central nervous system (e.g., spinal cord or brain). For example, electrical signaling, current, and/or stimulation may directly (e.g. through polarization or depolarization) or indirectly (e.g. through signaling cascades initiated or partially or fully blocked by electrical stimulation) result in a change in glial cell release of neuromodulators and cellular factors that sensitize (e.g., more excitable, more likely to fire or become activated) or dis-sensitize (e.g. make less excitable, less likely to fire or become activated) neurons to painful stimuli or otherwise modify the propensity to transmit pain signals from the periphery. As a non-limiting example, an embodiment of the present invention changes the number of non-neuronal cells using electrical stimulation, which relieves pain by creating or destroying non-neuronal cells.

Another method according to the present invention describes how an electrode is used to deliver a static or dynamic electrical field in, around, near, or within electrical proximity to a peripheral nerve that is not noticed by the patient (e.g., does not generate sensations, does not generate muscle contractions, does not generate noticeable afferent activity, and/or does not generate noticeable efferent activity) but is able to change the integrity and/or informational content of the neural signal being transmitted in the peripheral nerve, similar to how electrical static can (desirably or undesirably) change the integrity or signal quality of an electrical signal in a line or electrical wire without generating its own signal in the same line or wire (i.e., the static can be present without being noticed until a signal is transmitted or an attempt is made to transmit a signal through the electrical line). Such neural signals may include a pain or non-pain signal that are transmitted or attempt to be transmitted via the peripheral nerve in one or more Type III nerve fibers and/or Type IV nerve fibers or other fiber types (e.g., Type Ia, Type Ib, Type II) as the signal (e.g. one or more action potentials) travels, passes, or propagates by or near the region in which the electrode is generating the electric field.

The present device, system, and/or method to provide pain relief while avoiding direct activation of neural fibers is utilized in a way similar to or analogous to generating an electrical field (change in electrical potential either or both inside of and/or outside of neuronal and/or non-neuronal cells) that produces static or dynamic (i.e., non-static) interference that does not directly generate action potentials but changes the propensity or ability of or likelihood of a neural fiber to generate or propagate an action potential at its original rate or speed. As a non-limiting example, delivery of current via any form of electrical stimulation (e.g., charge, current, and/or voltage controlled stimulation) may change the electrical potential within or without (inside or outside) of a cell such that it changes the speed or propagation, timing, pattern, shape, features of one or more action potentials, which may in effect change the instantaneous, average, effective, or overall frequency (or neural information or neural code) of the neural signal and thereby change or reduce the sensation or perception of pain (e.g., by changing the way it is interpreted by the central nervous system (CNS) and/or how it is perceived in the brain of the patient).

Another method according to the present invention involves the generation of pain relief through the selective destruction of nerve fibers or selective death of nerve fibers using electrical signaling, current, and/or stimulation. Electrical stimulation or the generation of an electrical field in, around, near, or within electrical proximity to a peripheral nerve may cause selective death in peripheral nerve fibers (e.g. afferent fibers) that transmit painful signals, such as one or more Type III nerve fibers and/or Type IV nerve fibers or other fiber types (e.g., Type Ia, Type Ib, or Type II). As a non-limiting example of the present invention, delivery of current may change the electrical potential within or without (inside or outside) of a cell such that the concentration of ion(s) inside or outside the cell changes and/or the membrane potential (the electrical potential across the cell membrane) shifts sufficiently to activate or open voltage-sensitive ion channels and depolarize the cell to an extent or for a duration that initiates cell death (e.g., excitotoxicity, a process of damage or death of nerve cells that can occur with imbalance of ion concentrations inside the cell).

It is to be appreciated that examples of the present invention may be realized and achieved without and/or while avoiding neural damage or destruction of nerve fibers or death in peripheral nerve fibers.

Electrical stimulation may provide pain relief through the selective destruction of components, organelles, or structures inside or outside of nerve fibers or neuronal cells without the destruction or death of the nerve fibers or neuronal cells, including but not limited to ion channels, neuromodulatory substance receptors, myelin, or other internal, surface-bound, or external components of the neuronal cell. As another non-limiting example, destruction or modification of myelin caused by electrical stimulation in, on, around, or near a peripheral nerve fiber alters the propagation, conduction velocity, timing, pattern, and/or frequency of one or more action potentials that are transmitted through the nerve fiber past the location of myelin destruction or modification, possibly resulting in a change or reduction in the sensation or perception of pain (e.g., by changing the way it is interpreted by the CNS and/or how it is perceived in the brain of the patient). Existing techniques may use methods of ablation of tissue (e.g., radiofrequency ablation, cryoablation, cryotherapy, pulsed radiofrequency) to destroy part or all components of neural tissue, but these techniques are non-selective (e.g., for fiber type, fiber diameter, component of neural tissue). It is to be appreciated that the present invention is significantly different from existing techniques in that it is selective.

Whereas the foregoing methods generally rely on non-activating methods (e.g., delivery of electrical current, signals, or stimulation that do not activate nerve fibers), methods with some activation of afferent, efferent, or non-sensory fibers/structures) are also contemplated. In particular, another embodiment of the present invention includes delivering electrical stimulation that reduces the sensation of perception of pain by inducing action potentials in target neural structures at a frequency or pattern that does not cause a consciously perceived sensation, a consciously perceived muscle contraction, or other downstream effect of neural tissue activation (e.g., sub-threshold or sub-perception). As non-limiting examples, one or more action potentials may be generated in afferent nerve fibers whose effective frequency does not cause sensation, or stimulation may be applied with a pattern (e.g., low duty cycle, long rest periods between pulses of stimulation, stochastic and/or random stimulation pattern, or other appropriate pattern or lack thereof) that evokes action potentials in afferent fibers or efferent fibers that do not reach a threshold of perception of sensation or muscle contraction. Action potential generation or activation in non-nociceptive afferent neural fibers may inhibit, or "close the gate" to, the transmission of nociceptive pain signals to the brain.

Still further, the sensation or perception of pain can be reduced via electrical stimulation by inducing action potentials in target neural structures at a frequency or pattern that evokes a consciously perceived sensation that is non-painful and/or by inducing action potentials in target neural structures at a frequency that evokes sub-perception sensations. More particularly, this stimulation may evoke a normal sensation (i.e., is not paresthetic, abnormal, dysesthetic, or outside the range of sensations that are normally felt or perceived during normal sensory function). In contrast, previous techniques for pain relief relying on stimulation often use methods of electrical stimulation to activate peripheral nerve fibers and produce paresthesia (or abnormal sensations, or sensations that are comfortable but are not normally felt in the absence of electrical stimulation). However, the generation of paresthesia is not well-tolerated by some patients. Thus, to the extent some of the inventive methods described herein do not cause paresthesia or other consciously-perceived sensations, these non-painful, normal sensation techniques can present distinct advantages for specific patients.

As an example, the delivery of electrical stimulation can reduce the sensation or perception of pain by generating one or more action potentials in one or more efferent nerve fibers (e.g., A.alpha. or A.gamma. fibers) to produces contraction of one or more muscle fibers or bundles below the threshold for perception or sensation (i.e., subthreshold stimulation and pain relief). These muscle fiber(s) may be around, near, or in contact with a peripheral nerve such that contraction of the muscle fiber(s) may mechanically affect (e.g., compress, stretch, displace, or other mechanical interaction) the peripheral nerve to alter transmission of one or more action potentials in one or more nerve fibers. Mechanical stimulation of nerve fibers may alter (e.g., increase or decrease) conduction velocity or propagation time of one or more action potentials, change or alter the timing, frequency, or pattern of one or more action potentials, or otherwise alter a transmitted signal (or neural information or neural code) of the neural signal and thereby change or reduce the sensation or perception of pain (e.g., by changing the way it is interpreted by the CNS and/or how it is perceived in the brain of the patient).

Yet another method according to this embodiment of the present invention involves delivering electrical signals, current and/or stimulation in, around, near, or within electrical proximity to a non-sensory neural structure to generate one or more action potentials in the neural structures that results in a decrease in the sensation or perception of pain without producing a conscious sensation or perception of the stimulation. Although the delivery or electrical signals, current and/or stimulation is in, around, near, or within electrical proximity to a neural structure, it is to be appreciated that the device and/or system may be located remote to, away from, or in, around, near, or within physical proximity to the neural structure (e.g., the electrode(s) may be close and/or far from the neural structure and the invention will still be able to achieve the desired effect). As a non-limiting example, stimulation may generate one or more action potentials in neural structures that are components of the autonomic nervous system, including autonomic, sympathetic, or parasympathetic nerve fiber(s), cell bodies, or ganglia, resulting in modulation (e.g., increase or decrease, up-regulation or down-regulation) of autonomic control of one or more bodily functions not under conscious control. Here, stimulation that generates one or more action potentials in autonomic neural structures may result in vasoconstriction or vasodilation, or the contraction or relaxation of smooth muscle in vasculature or blood vessels, such that blood flow (or supply) to an area of the body may increase or decrease. Changes in blood flow (or supply) may, as a non-limiting example, mechanically affect a peripheral nerve and alter transmission of signals along the nerve (e.g., as may occur in a neurovascular bundle where one or more peripheral nerves lie adjacent to or in close proximity to one or more blood vessels, and contraction or expansion of a blood vessel may mechanically impact, compress, or stretch a nerve), or alter transmission in nerve fibers by changing the supply of ion(s), neurotransmitters, neuromodulatory substances, oxygen, carbon dioxide, energy (e.g., glucose), and other materials delivered through the vasculature.

In any of the foregoing inventive methods, the electrical stimulation is preferably applied outside of the central nervous system (e.g., the spinal cord or brain) or the dorsal root ganglia (DRG). Thus, the associated devices, systems, and methods \function effectively without the need to place an electrode in proximity to the CNS, including the brain and/or spinal cord, or the DRG.

In one embodiment of the present invention, electrical stimulation in the periphery modulates non-neuronal cell activity (e.g., glial cell activity) that changes neuronal transmission (or activity or neural information) to provide pain relief, and the change of neuronal transmission (or activity or neural information) can be effected without or prior to changes in synaptic transmission and/or be effective in modulating pain without direct glial cell modulation of synaptic activity in the central nervous system (e.g., spinal cord or brain) or the DRG. Synaptic activity may be modulated, but it may be modulated only as a result of the modulation of axonal activity caused by changes in non-neuronal cell function or activity.

As a non-limiting example, peripheral nerve stimulation and/or delivery of electrical signals, current, and/or stimulation in the periphery may be accomplished by the invention in a way that is not perceived while still affecting glial or other supporting cells in the peripheral nervous system and/or the central nervous system to reduce pain In a further embodiment, electrical stimulation delivered in the region of one or more peripheral nerve modulates the excitability and/or the firing activity of one or more nerve fibers within the peripheral nerve. The modulation can occur through direct effect on the nerve fiber(s) by the effect of the electric field on the intra and/or extracellular fluid or ion concentrations, thereby impacting the nerve membrane and the ion channels which determine the conduction properties of the nerve fiber(s). The modulation can also occur through indirect effect on the nerve fiber(s) by the effect of the electric field on one or more non-neuronal cells (e.g., glial cells) which then impact the excitability of the nerve fiber(s). Through direct or indirect actions, the action potential firing characteristics of the nerve fiber(s) can be influenced via stimulation such that the neuronal signaling which is conducted into the central nervous system (e.g., spinal column and brain) avoids the continuation of the painful signals from the periphery.

In another embodiment, the changed firing patterns interrupt the central sensitization process in the central nervous system, disrupting the self-sustaining path of chronic pain. These changed firing patterns may additionally or alternatively provide the central nervous system with signals that convey non-painful and/or healthy signaling from the periphery. In any case, such signaling can influence important "pain structures" in the central nervous system that contribute to excess nerve excitability and the cycle of chronic pain. These "pain structures" include (but not limited to) structures and/or cells such as glial cells, which may be put into a "primed" or "excitatory" state when signals associated with chronic pain are received from the periphery, but they can also be returned to a "resting" or "healthy" state with alternative signal input from the periphery such as that provided by sub-threshold or non-perceived stimulation in the periphery.

It is to be appreciated that the presently proposed devices, systems, and methods can function effectively without (and/or independent of) cell therapy (or methods, devices, or systems that are used for cell therapy). For example, the proposed devices, systems, and methods are designed to be effective independent of (and without needing to cause or influence or prepare) changes to fully or partially undifferentiated cells (e.g., naturally occurring or for implantation) and independent of (and/or without the need or requirement of) changing the differentiation of the fully or partially undifferentiated cells. It is also to be appreciated that the presently proposed devices, systems, and methods can function effectively without (and/or independent of) implanted cells, such as cells implanted in the nervous system of elsewhere. The use of implanted cells is not required as part of the present invention.

Further, the inventive devices, systems, and methods can function effectively without (and/or independent of) promoting directional growth and connectivity of neural cells near the device or its components, such as the electrode(s) (e.g., anode(s) and/or cathode(s)).

One embodiment of the present invention is the use of electrical stimulation at levels that do not generate action potentials to enhance the effects of other pain therapies. These therapies that could be used in conjunction with electrical stimulation may include, but are not limited to, oral medications, physical therapy, and injections. Existing therapies that generate action potentials (e.g., experienced as parenthesis, muscle contractions, or other sensations) may be distracting or uncomfortable to patients. Also, existing therapies utilizing electrical stimulation do not relieve pain by increasing the analgesic effect of other concomitant therapies.

One embodiment of the present invention is the use of electrical stimulation to alter gene expression, which results in relief of pain. The stimulation may initiate, increase, decrease, or stop gene expression. This change in gene expression may impact the production of endongenous substances, neurotransmitters, receptors for neurotransmitters or neuromodulatory substances, ion channels, and/or other proteins involved in the propagation of action potentials or synaptic transmission (e.g., synaptic and vesicular proteins). The electrode is placed remote to the nerve to avoid activation, but is able to alter gene expression in the vicinity of the nerve. Existing methods of delivering electrical stimulation require intimate nerve contact, which limits the spread of current before activation of axons, resulting in a limited extent of gene expression. Also, existing methods may deliver electrical stimulation superficially (i.e., through the surface of the skin), and activation of cutaneous fibers may cause irritation or discomfort and limit the amount (e.g., intensity) of current delivered, thus limiting the degree of change to gene expression.

One embodiment of the present invention is the use of a stimulating lead or electrode placed in the vicinity of neuronal structures (e.g., axons) to generate an encapsulation response around the lead or electrode, which relieves pain through the increased concentration of substances involved in the encapsulation process. Indwelling leads or electrodes are treated as foreign bodies, and a foreign body response is triggered. As a non-limiting example, the processes of the foreign body response (e.g., protein adsorption, macrophages, foreign body giant cells, fibroblasts, angiogensesis) affect the nearby neuronal structure, resulting in pain relief. The remote placement of the lead from the nerve enables the foreign body response to generate pain relief without negatively impacting the nerve fiber. Existing techniques that involve intimate placement of the electrode or lead on a nerve may generate foreign body responses (e.g., tissue encapsulation), but their close proximity to the nerve may damage or impair the nerve, and may also cancel out the beneficial effects of the foreign body response. Other existing techniques of electrical stimulation that place electrodes very far from the nerve target (e.g., greater than 1 cm, 5 cm, and/or 10 cm) may be too far from the nerve for the foreign body response to interact with the nerve and provide pain relief.

One embodiment of the present invention is the use of electrical stimulation to increase the temperature around a neuronal structure (e.g., axon) to relieve pain without directly generating action potentials. In one non-limiting example, the change in temperature alters the dynamics of the ion channels in the neuronal membrane, which impacts waveform shape and/or stimulation pulse frequency and/or pattern.

The systems and methods of deploying the same are generally shown in FIGS. 6A through 7E. Publications 20100152808 and 20120310301 are for examples of systems that may be adjusted to deliver subthreshold pain relief according to certain aspects of the invention described herein.

These types of devices, systems, and methods to provide pain relief when the device or system or a component of the device or system, such as one or more electrodes are placed on, in, or near a peripheral nerve, neuronal cells, and/or non-neuronal cells. It is also possible to provide pain relief when the device or system or a component of the device or system, such as one or more electrodes, are placed remote or far from a peripheral nerve, neuronal cells, and/or non-neuronal cells. The device or system, or a component of the device or system, such as one or more electrodes, may be placed spatially (or mechanically) remote or far (in terms of physical or anatomical distance) from while being in electrical proximity (or sufficiently close) to a peripheral nerve, neuronal cells, and/or non-neuronal cells to, as a non-limiting example, change the level of polarization or membrane potential of a non-neuronal cell such as a glial cell or other non-neuronal cell outside of the CNS and outside of the DRG. Placing the electrode remote (e.g., 5 mm to 30 mm, 1 mm to 50 mm, and/or 0.01 mm to 100 mm) from the peripheral nerve may enable a greater intensity of stimulation to be delivered before producing discomfort from activation of fibers in the nerve trunk or local nerve fibers, enabling a greater volume of tissue (and greater number of non-neuronal structures) to be exposed to the electrical stimulation. Placing the electrode remote from the peripheral nerve may enable non-neuronal cells on the opposite side of the nerve to be stimulated, enabling more uniform distribution of stimulation of non-neuronal cells around the circumference of the nerve trunk.

Desirably, one embodiment of the device and system utilizes an electrode that is designed to anchor in tissue, such as tissue other than that of the peripheral nerve (e.g., muscle, adipose, connective, or other tissue) and deliver electrical current that can affect non-neuronal or neuronal cell function and/or activity and produce pain relief. In one embodiment, the electrode or electrodes may be incorporated into a coiled, helical, and/or open-coiled lead of a small (e.g., 0.1-0.8 mm, 0.01-1.5 mm, 0.001-5 mm) that desirably reduces movement of the electrode in the tissue. Such a lead may also desirably reduce the risk of infection.

These devices, systems, and methods can also provide pain relief through electrical stimulation at intensities below the thresholds for activating nerve fibers. These thresholds may vary depending on the physical location of the electrode(s) relative to the peripheral nerve or neuronal cells. Sensations and/or motor responses may be generated through activation of nerve fibers at larger intensities than those required for pain relief, and may serve as a confirmation tool or range-finding tool or technique for identifying the threshold for sensation or motor response, or to indicate that the stimulation intensity is sufficient for pain relief (although activation of nerve fibers is not responsible for the pain relief).

They may deliver optimal frequency(ies) of electrical current designed to maximize pain relief and/or minimize unwanted changes in other neuronal activity (e.g., minimize alterations in sensations and/or muscle contractions). Optimal frequency(ies) of electrical current may also be designed to maximize pain relief and/or minimize unwanted changes in afferent activity and/or efferent activity in the peripheral nerve fiber(s). It is possible for the device, system, and method to provide pain relief when electrical current is delivered at any average frequency, including low (e.g., 1 Hz or <1 Hz) and high (e.g., 10 kHz, 20 kHz, or >20 kHz) and any other frequency.

Figure 2:
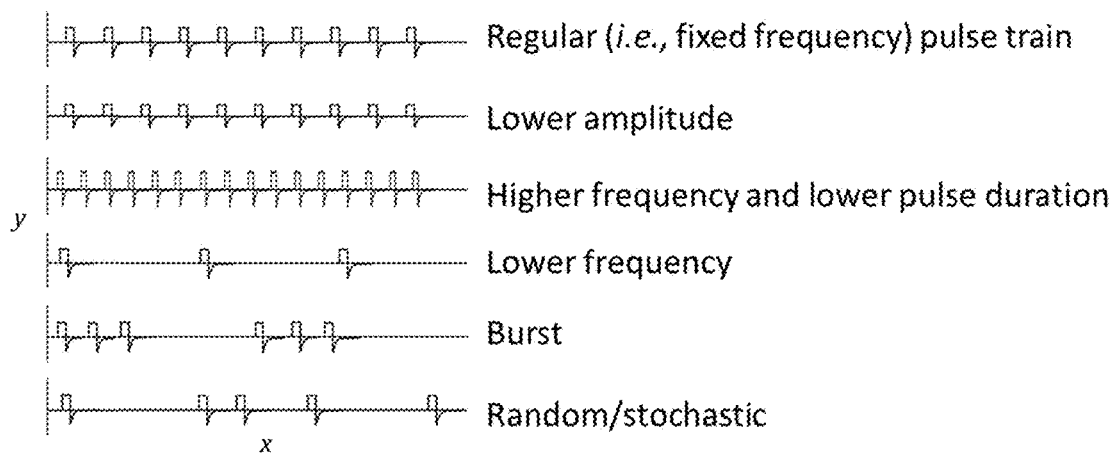
FIG. 2 are exemplary schematics of electrical signal patterns that can be delivered in a sub- or supra-threshold manner, so as to be perceived as normal or undetected to facilitate the reduction of pain according to certain aspects of the invention, with the y-axis representative of relative amount of stimulus intensity applied and the x-axis representative of the passage of time.
Figure 3:
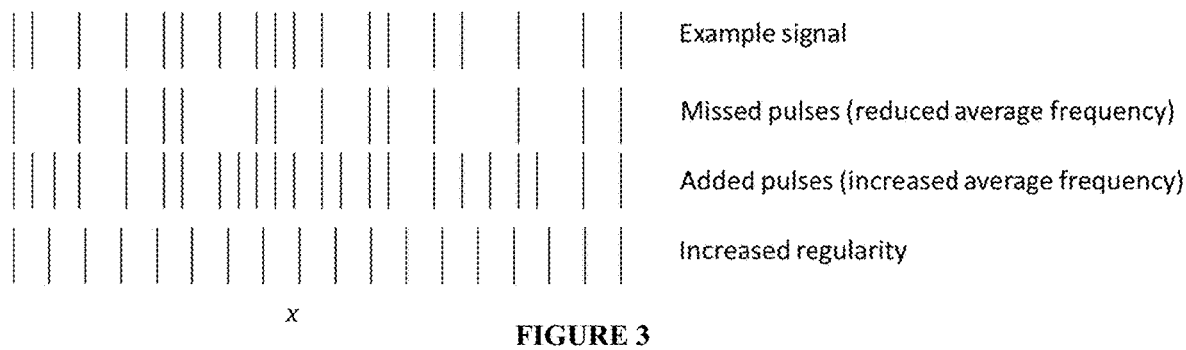
FIG. 3 are exemplary of nerve firing patterns that can be produced directly through stimulation/modulation according to certain aspects of the invention, with the x-axis representative of time and the individual vertical lines in each series representative of an action potential.
Figure 4:
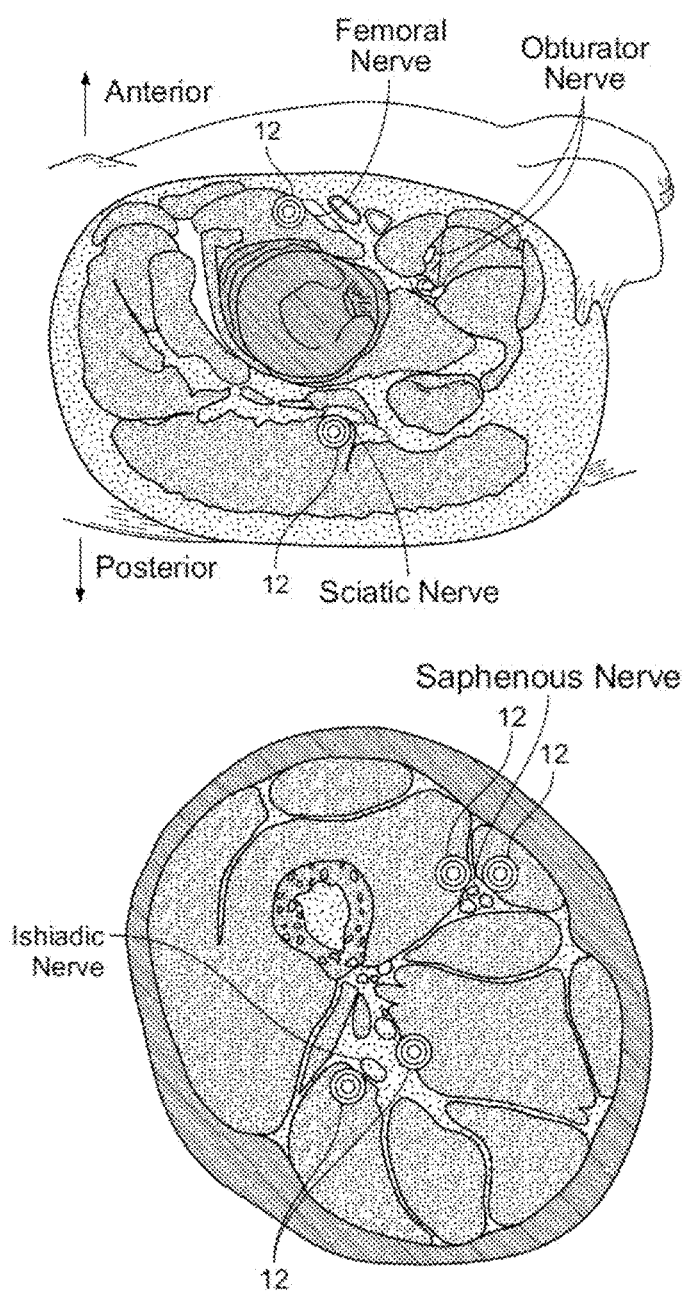
FIG. 4 are cross sectional top plan illustrations in which the circles 12 indicate where lead(s) may be placed proximate to or remote from one or more peripheral nerves according to certain aspects of the invention.
Figure 5:
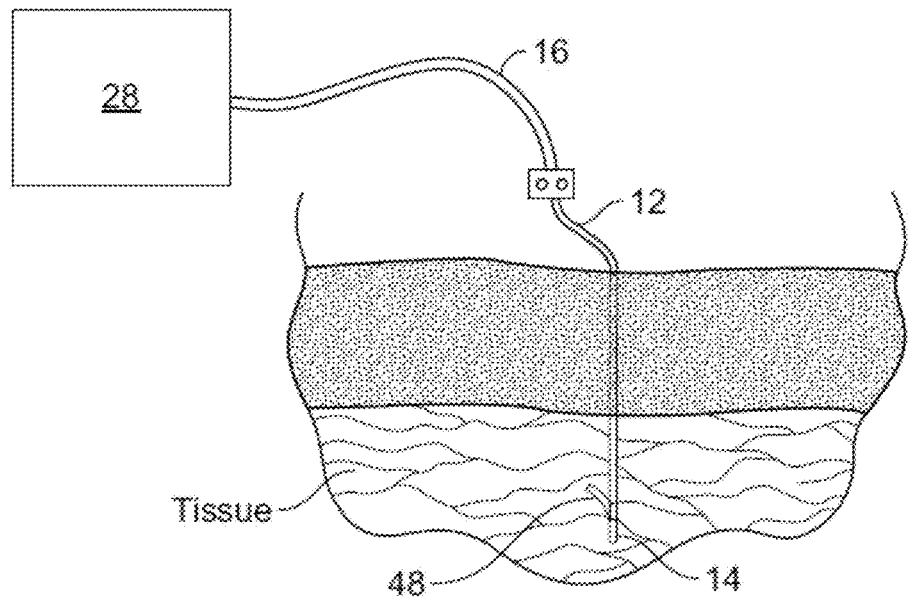
FIG. 5 is a cross sectional, exemplary side view of a the stimulator and lead for delivering stimulation according to certain aspects of the invention.
Figure 6A:
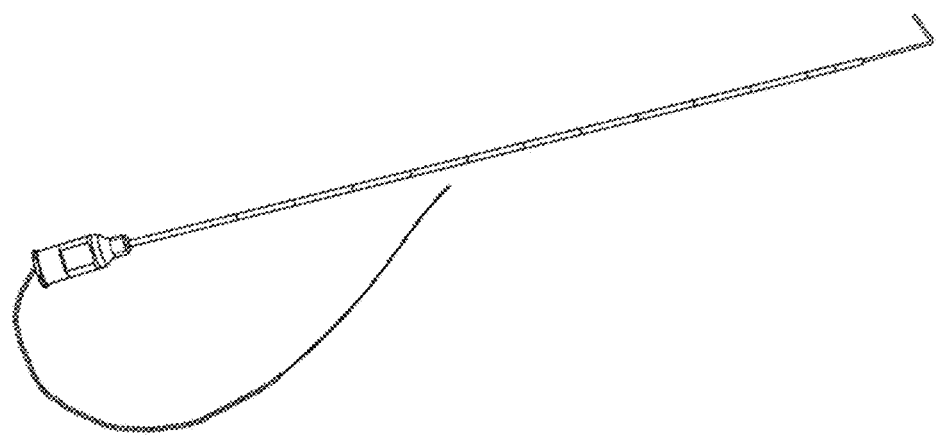
FIGS. 6A and 6B are perspective photographic depictions of the lead and stimulator, respectively speaking, according to certain aspects of the invention.
Figure 6B:
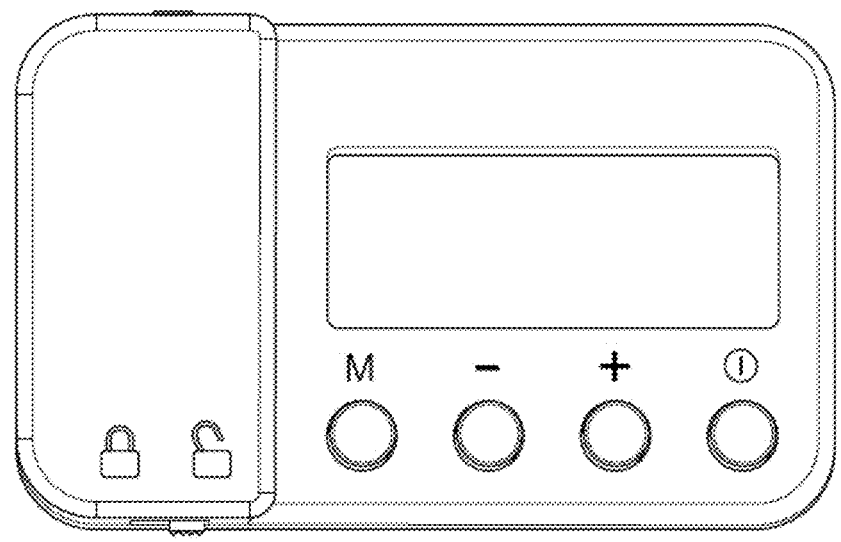
Figure 7A:
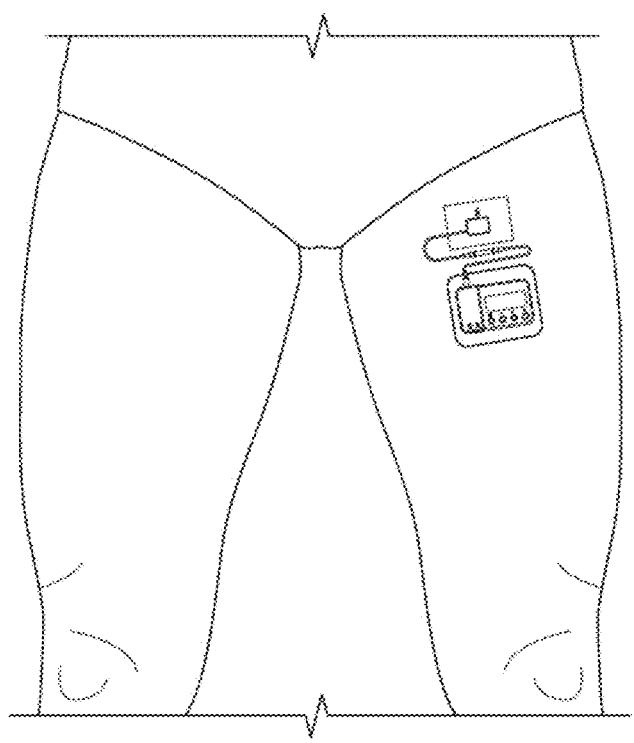
FIGS. 7A through 7E are plan view illustrations of exemplary areas on the body wherein the stimulator and lead may be positioned according to certain aspects of the invention.
Figure 7B:
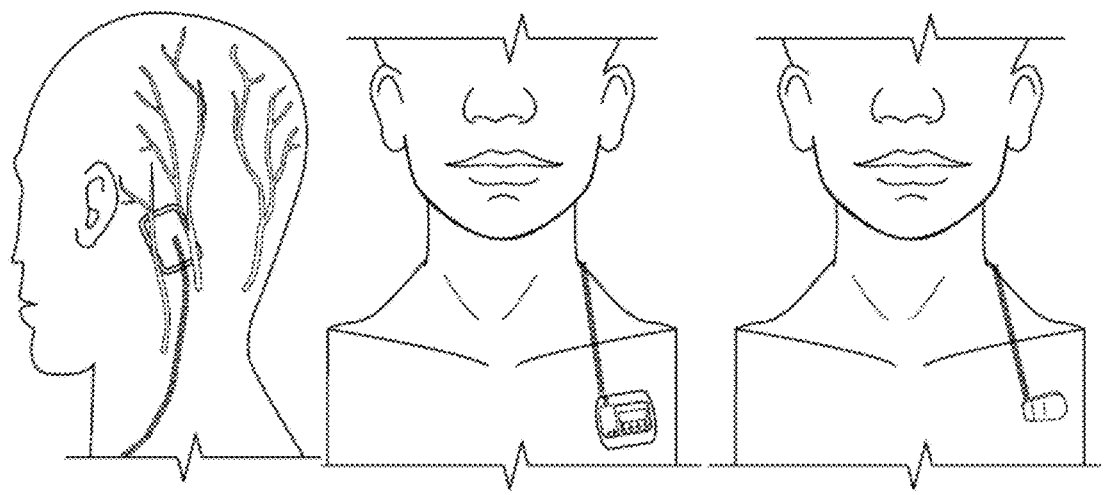
Figure 7C:
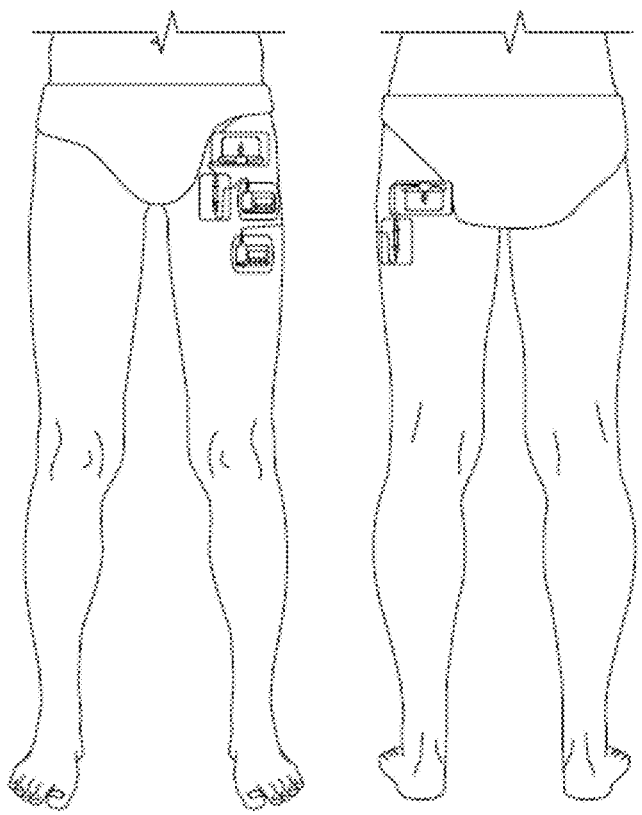
Figure 7D:
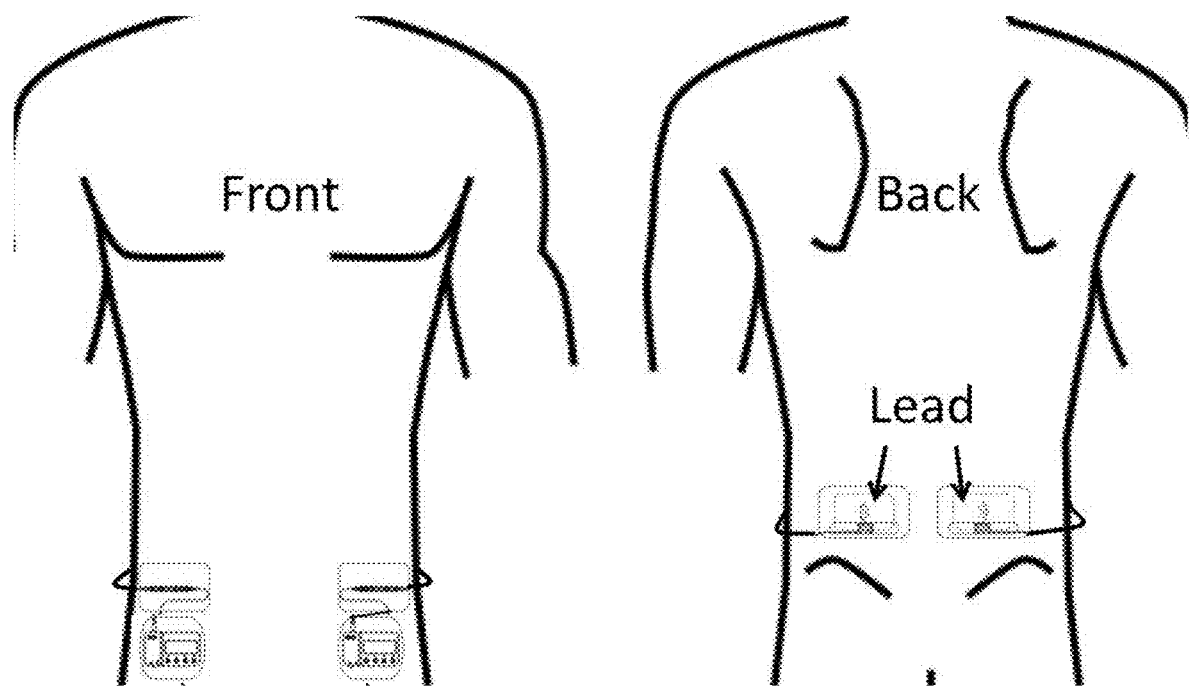
Figure 7E:
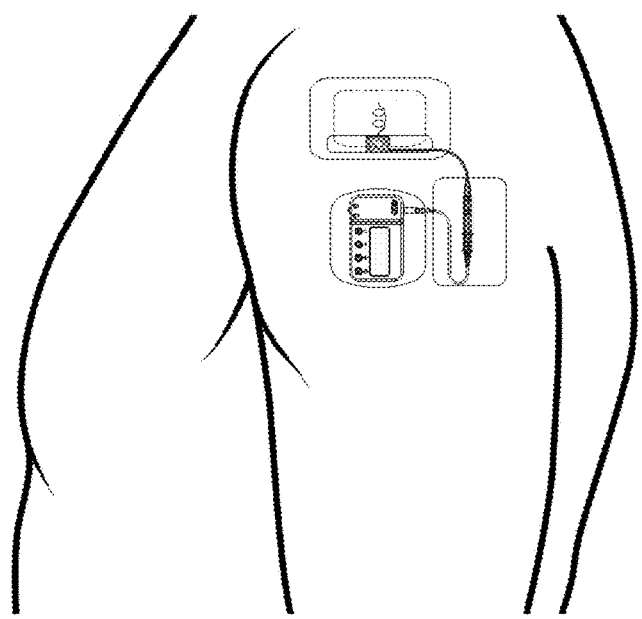

With reference to FIG. 2, the stimulation pattern may be regular (all stimulation pulses delivered at the same rate with the same interpulse interval), random or stochastic (e.g., white or pink noise), burst (e.g., group(s) of finite number of pulses delivered with some interpulse interval and each group is separated by a longer interburst interval), or other pattern. The stimulation pattern may be a biomimetic (directly mimicked) signal based on a biologic signal. Biomimetic patterns may be predetermined based on or in response to recorded and/or analyzed afferent neural activity obtained directly from the animal to be relieved of pain or obtained directly from an animal that is not the animal to be relieved of pain (live model), may be calculated or modeled from one or more patterns obtained from one or more animals (including or excluding the animal to be relieved of pain), and/or may be mathematically or otherwise artificially generated (i.e., without sampling).

The stimulation pulse may include, but are not limited to, monophasic, biphasic, and/or multiphasic. The pulse may be any shape, including but not limited to rectangular, sinusoidal, trapezoidal, exponential, irregular, and/or combinations or variations of waveforms with one or more positive and/or negative phases or portions. In the case of the biphasic or multi-phasic pulse, the pulse may be symmetrical (e.g., both the positive and negative phases have equal amplitude, pulse duration, shape, etc.) or asymmetrical (e.g., the positive and negative phases may differ in terms of amplitude, pulse duration, shape, etc.). It is possible for the device, system, and method to provide pain relief when electrical current is delivered with the above waveform phases, shapes, and symmetries at any average frequency, including low (e.g., 1 Hz or <1 Hz) and high (e.g., 10 kHz, 20 kHz, or >20 kHz) and any frequency in between the two extremes. Waveforms do not necessarily have to be charge-balanced (i.e., charge delivered during positive and negative phases do not need to be equal). Waveforms that are not charge-balanced may enable accumulation of charge on electrodes (e.g., cathode and/or anode) and affect the electrical, ionic, and/or chemical (e.g., pH, neurotransmitter) environment around the electrode and/or nerve.

The peripheral nervous system of an animal generally comprises efferent and afferent neural fibers, and prior pain reduction modalities have focused on action potential generation or activation in non-nociceptive afferent neural fibers to inhibit, or "close the gate" to, the transmission of nociceptive pain signals to the brain. This has come to be known as the gate control theory of pain management. Most afferent fibers, however, are not bundled only with other afferent fibers; rather, the majority of nerves found amenable to peripheral nerve stimulation are nerve bundles comprising both afferent and efferent fibers. Electrical stimulation may also mediate pain relief by activating somatosensory pathways that may be associated with mechanoreceptors, thermoreceptors, proprioceptors, and/or chemoreceptors. Generally, types of neural cells, axons, nerve fibers, or physiological structures that may be affected, such as by intra- or extra-muscle (e.g., in subcutaneous, connective, adipose, or other tissue) electrical stimulation, include functional afferent types A and C axons and efferent type A axons. In addition to these methods and the systems used to accomplish these methods, the delivery of electrical current, signal(s), and/or stimulation provided according to systems and methods of the present invention may also provide pain relief, reduce pain, control the amount of pain that is perceived, and/or completely eliminate pain without activation or excitation (e.g., while avoiding direct activation and/or excitation) of peripheral nerve fibers (e.g., including avoiding activation of afferent fibers, such as type I, II, III, and/or IV fibers, and/or efferent fibers, such as alpha and/or gamma (e.g., A.alpha. and/or A.gamma) fibers) and while avoiding undesirable block of peripheral nerve fibers (e.g., including avoiding block of afferent fibers, such as type I, II, III, and/or IV fibers, and/or efferent fibers, such as alpha and/or gamma (e.g., A.alpha. and/or A.gamma) fibers).

As a non-limiting example, the present invention may reduce the perception of chronic or persistent pain (e.g., background pain), such as pain that may be unrelated to the health of the tissue in which the pain is perceived, including pain that persists after an injury has healed or after a disease state has resolved (e.g., pain that does not or no longer benefits the patient, does not serve a beneficial function, is not functional, is not useful, and/or does not warn the patient of potential or real tissue damage such as new or additional tissue damage or a change in disease state), while desirably avoiding the reduction and/or block of acute, temporary, and/or transient pain that correlates to a new, acute, temporary, changing, progressing, advancing, increasing, and/or transient noxious stimulus(i) and/or a new, acute, temporary, changing, progressing, advancing, increasing, and/or transient potential or real tissue damage or disease state (e.g., avoids blocking pain that does benefit the patient, serve a beneficial function, is functional, is useful, and/or warn the patient of potential or real tissue damage such as new or additional tissue damage or a change in disease state). The present invention may reduce the perception of chronic, persistent, background, and/or non-functional pain without blocking new, changing, acute, and/or functional pain by delivering electrical current, signal(s), and/or stimulation that influences neural structures, cells or parts of cells that support, maintain, or influence the function of nerve cells and/or their components. The present invention may reduce the perception of chronic, persistent, background, and/or non-functional pain without blocking new, changing, acute, and/or functional pain by delivering electrical current, signal(s), and/or stimulation that influences neural structures, cells or parts of cells that support, maintain, or influence the function of nerve cells and/or their components while avoiding and/or without generating action potentials (e.g., without exciting the nerve cells to the point that action potentials are generated) and/or without generating action potential(s) in a way that causes sensations, paresthesias, and/or muscle contractions and/or muscle activation. As a non-limiting example, the present invention may deliver electrical current, signal(s), and/or stimulation such that the function and/or state of one or more glial cells is altered which changes the properties of one or more axons, nerve fibers, or other nerve cell components (for a short and/or long duration, including temporarily, transiently, short-term, permanently and/or long-term) such that the generation, propagation, transmission, and/or other characteristics of neural signaling (e.g., changing the instantaneous, effective, average, or overall frequency of one or more action potentials; changing a probability of one or more action potentials occurring; changing excitability of at least one nerve; and/or changing conduction velocity, shape, form, features, interpulse interval, period, rate, coefficient of variation, or duration of one or more action potentials and/or changing timing, spacing, or pattern of one or more action potentials or trains of action potentials) are altered such that the perception of pain by the central nervous system is reduced. This effect of pain reduction can be achieved without generating action potentials and without blocking action potentials, and it can be achieved while avoiding generating action potentials and while avoiding blocking action potentials. As a non-limiting example, avoiding generating action potentials avoids the generation of paresthesia. As a non-limiting example, avoiding blocking action potentials, avoids preventing the patient from perceiving acute, temporary, and/or transient pain (e.g., enables and/or facilitates reduction of unwanted (or non-functional) pain while enabling and/or facilitating the perception of desirable (or functional) pain and/or other desirable sensations (or sensory functions) and/or facilitating desirable muscle activation (or efferent functions)).

The amount and/or degree to which functions, attributes, and/or states of neural support structures and/or cells may be altered, modified, or changed can be controlled and/or titrated (e.g., to directly or indirectly produce more or less inhibition without or while avoiding causing either excitation sufficient to generate an action potential or inhibition sufficient to cause complete block or partial block if partial block is undesirable). As a non-limiting example, the delivery of electrical current, signal(s), and/or stimulation may bias, predispose, dispose, and/or influence the nerve, in whole or in part, the neuronal structures, neuron and/or its components such that unwanted signals in a given nerve fiber are filtered but the nerve fiber is not blocked indiscriminately, entirely, or in a way that is undesirable.

As a non-limiting example, the present invention can within a given nerve fiber, axon, cell body, soma, dendrite, and/or other individual component or combination of neural components (or across a network of 2 or more neurons or their components, such as a synapse) filter selectively and/or tune out selectively neural signals that are undesirable while enabling neural signals that are desirable to be transmitted. The present invention has advantages over prior methods and systems for blocking nerves in which the prior inventions have focused on either blocking nerve or nerve fibers that carried unwanted (e.g., pain) signals or signals that would cause a perception of pain. The present invention teaches how to filter a given nerve fiber(s) according to qualities or characteristics of the pain signal within that fiber(s), such that a dull pain may be reduced but a sharp pain may be facilitated or vice versa, a low intensity constant pain may be reduced but a high intensity transient or rapidly changing pain may be facilitated or vice versa. It is to be appreciated that while the type of fiber through which one or more action potentials is transmitted is one variable which influences how that neural signal of one or more action potentials is interpreted and perceived, the type of fiber is not the only variable. The present invention takes advantage of and modulates multiple variables to reduce pain while avoiding reduction of desirable functions and perceptions and avoiding the generation of unwanted functions, such as unwanted muscle contractions, and unwanted sensations, such as parenthesis. Changes occur following injury(ies), surgery(ies), initiation and/or progression of disease states, including but not limited to changes in neural connections, neural networks, firing patterns, transmission properties, and/or other characteristics of neural signaling that can lead to an increase in undesirable pain, non-beneficial, and/or non-functional pain. As a non-limiting example, during a hyper-sensitized state (e.g., following injury(ies), surgery(ies), initiation and/or progression of disease states) changes (e.g., in inter-neuron connections, formation of new synapses, and/or strengthening or weakening of existing synapses) can occur such that a fiber which would in a normal state transmit signals that would be perceived as comfortable would in a hyper-sensitized state transmit signals that would be perceived as uncomfortable or painful. The same fiber may also still (even in the hyper-sensitized state) also transmit signals that are desirable, useful, and/or functional and perceived as comfortable, and the perception may depend on the characteristics of the signal that is transmitted. Thus, blocking this fiber to reduce pain would also block the transmission of the signals that are desirable, useful, and/or functional. Generating action potentials within this fiber to reduce pain could generate parenthesis, which may be undesirable. To address these challenges while still reducing pain, the present invention can deliver electrical current, signal(s), and/or stimulation such that the undesirable signals are filtered or altered while avoiding block of the desirable signals. By filtering the neural signals within a given or selected fiber or neuron or group of fibers or group (or network) of neurons, the present invention can effect long-lasting changes in the nervous system such that pain relief is long-lasting or permanent such that the device can be removed (or intentionally deployed only transiently for a temporary or short duration) while the pain relief continues and is sustained. Alternatively, it can enable intermittent (e.g., with a set, variable, random, or pseudo-random duty cycle of off and on and/or with changing intensities) delivery of electrical current, signal(s), and/or stimulation with a short-term or long-term or a temporary or a permanent system (e.g., that is more efficient and/or has an improved or increased effect with the intermittent cycling of stimulation).

By delivering electrical current, signal(s), and/or stimulation to the peripheral nervous system, the present invention can cause changes that are temporary or permanent in the peripheral nervous system, the central nervous system, and in the interactions between the peripheral nervous system and the central nervous system. As a non-limiting example, the present can encourage or discourage the growth, strengthening, reduction, and/or weakening of new and existing connections, synpases, and/or transmission patterns and/or signals. The present invention can encourage or discourage the growth, strengthening, reduction, and/or weakening of new and existing connections, synpases, and/or transmission patterns and/or signals by changing the environment in which a nerve cell operates and functions directly and/or indirectly by changing the support structures and cells that have the potential to maintain and/or change the environment in which a nerve cell operates and functions.

The afferent axons may be classified as A.alpha. (type Ia or Ib), A.beta. (type II), A.delta. (type III), or C (type IV). A.alpha. (type Ia) fibers are generally recognized as being associated with the primary sensory receptors of the muscle spindle, such as for transducing muscle length and speed. These fibers are myelinated, usually having a diameter from about 9 to about 22 micrometers (.mu.m), although other diameters have been observed and may be included, and a conduction velocity of about 50 to about 120 meters per second (m/s), which is known to be proportional to the diameter of the fiber for both this type and other types of myelinated fibers. A.alpha. (type Ib) fibers are generally recognized as being associated with Golgi tendon organs, such as for transducing muscle contraction. These fibers are myelinated, having a diameter from about 9 to about 22 micrometers (.mu.m) and a conduction velocity of about 50 to about 120 meters per second (m/s). A.beta. (type II) fibers are generally recognized as being associated with the secondary sensory receptors of the muscle spindle, such as for transducing muscle stretch. These fibers are also associated with joint capsule mechanoreceptors (as transduces joint angle) and all cutaneous mechanoreceptors. The cutaneous mechanoreceptors may include Meissner's corpuscles, Merkel's discs, Pacinian corpuscles, Ruffini corpuscles, hair-tylotrich (for sensing stroking/fluttering on the skin or hair), and the field receptor (for sensing skin stretch). The present invention can reduce pain while enabling desirable sensations from afferent fibers to be perceived.

Meissner's corpuscles are nerve endings that can be found in the skin, which transmit afferent information regarding touch (such as soft, or light, touch) and/or vibration, especially at vibration frequencies of less than 50 Hertz. These fibers are rapidly adaptive receptors that are often located below the epidermis within the dermal papillae. The corpuscles may be found as encapsulated unmyelinated nerve endings, comprising flattened supportive cells arranged as horizontal lamellae surrounded by a connective tissue capsule. Examples of this corpuscle have been described as having a length of about 30 to about 140 .mu.m and a diameter of about 40 to about 60 .mu.m.

Merkel's discs are a type of mechanoreceptor found in the skin, hair follicles, and in the oral and anal mucosa. The discs transmit afferent information regarding pressure and texture. Sometimes referred to as a Merkel disc receptor or Merkel cell-neurite complex, the nerve ending comprises a Merkel cell next to a nerve terminal. A single afferent nerve fiber may innervate multiple nerve endings, such as 50-100 endings. This mechanoreceptor is an unencapsulated, slowly adapting type I mechanoreceptor that will provide a non- or minimally-decaying response to pressure. The Merkel disc receptor may have two phases of firing, dynamic and static. In the static phase, an irregular activity may be observed, which may be typical of slowly adapting type I mechanoreceptors but contrasts with the regular pattern of slowly adapting type II mechanoreceptors.

Pacinian corpuscles are nerve endings that may be found in the skin. They may also be found in the mesentery, between layers of muscle, and on interosseous membranes between bones. Pacinian corpuscles transmit afferent information regarding pain and pressure. For instance, these corpuscles may detect gross pressure changes and vibrations and may fire in response to quick changes in joint position. They are phasic tactile mechanoreceptors that can detect deep pressure because they are found below the skin surface, usually in the dermis, and comprise some free nerve endings.

Ruffini corpuscles are slowly adapting mechanoreceptors that may be present in the glabrous dermis (hairless skin) and subcutaneous tissue of humans. These corpuscles transmit afferent information regarding skin stretch, movement, position (such as position of the fingers), and sense of control (such as slipping of objects along the skin surface). This type of receptor may have a spindle shape, and they may be found in the deep layers of the skin, allowing them to indicate continuous pressure states and mechanical joint deformation, such as joint angle change.

The A.beta. fibers are myelinated, usually having a diameter from about 6 to about 12 micrometers (.mu.m), although other diameters have been observed and may be included, and a conduction velocity of about 33 to about 75 meters per second (m/s).

A.delta. (type III) fibers are generally recognized as being associated with free nerve endings of touch and pressure (for sensing excess stretch or force), hair-down receptors (for sensing soft, or light, stroking), nociceptors of the neospinothalamic tract, and cold thermoreceptors. These fibers are thinly myelinated, having a diameter from about 1 to about 5 micrometers (.mu.m) and a conduction velocity of about 3 to about 30 meters per second (m/s).

C (type IV) fibers are generally recognized as being associated with nociceptors of the paleospinothalamic tract, and warmth thermoreceptors. These fibers are unmyelinated, having a diameter from about 0.2 to about 1.5 micrometers (.mu.m) and a conduction velocity of about 0.5 to about 2.0 meters per second (m/s).

As mentioned above, most nerve bundles include both afferent and efferent fibers. The efferent axons may be classified as A.alpha. or A.gamma. A.alpha. efferent fibers are generally recognized as being associated with extrafusal muscle fibers. These fibers are myelinated, having a diameter from about 13 to about 20 micrometers (.mu.m) and a conduction velocity of about 50 to about 120 meters per second (m/s). A.gamma. efferent fibers are generally recognized as being associated with intrafusal muscle fibers. These fibers are myelinated, having a diameter from about 5 to about 8 micrometers (.mu.m) and a conduction velocity of about 20 to about 40 meters per second (m/s).

A first method according to the present invention includes avoiding activating afferent fibers (e.g. type Ia, Ib, and/or II, which may also be called A.alpha. and/or A.beta. afferent fibers), which are physically located in an area from or in which an animal is perceiving pain. When a fiber is referred to herein as "activated," it is to be understood that at least one action potential is generated or initiated by or along, or propagated along, such fiber in response to some form of stimulation. While such afferent fiber activation may mediate pain relief by activation of afferent pathways associated with primary receptors of muscle spindles, Golgi tendon organs, secondary receptors of muscle spindles, joint receptors, touch receptors (e.g. Meissner's corpuscles, Merkel disk receptors, Pacinian corpuscles, Ruffini endings, etc.) other types of mechanoreceptors (e.g. joint capsule mechanoreceptors), and/or proprioceptors, the present invention can mediate pain relief while avoiding such activation and avoiding the generation of paresthesia while enabling these fibers to continue to transmit signals that are meaningful and desirable. As a non-limiting example, delivery of electrical current, signal(s), and/or stimulation may provide pain relief while still enabling or facilitating one or more A.beta. fibers that carry afferent information from a mechanoreceptor (i.e. a sensory receptor) that responds to mechanical pressure or distortion to transmit the desired signal without blocking it. The electrical current, signal(s), and/or stimulation may be applied in muscle, in non-muscle tissue (e.g. subcutaneous, connective, adipose or other tissue), and/or to neural and related tissue. Non-limiting examples of mechanoreptor pathways that may be desirable uninhibited (e.g. not blocked) by delivery of electrical current, signal(s), and/or stimulation include (1) one or more Pacinian corpuscles; (2) one or more Meissner's corpuscles; (3) one or more Merkel disc receptors; and/or (4) one or more Ruffini corpuscles. The applied electrical current, signal(s), and/or stimulation may mediate pain relief through the modulation of fibers carrying signals interpreted as painful (e.g., filtering specific signals and/or down-regulating certain activity without completely blocking it) and/or through the modulation of fibers carrying signals interpreted as comfortable (e.g., filtering specific signals and/or up-regulating certain activity without completely blocking it or generating parenthesis) in nerve fibers associated with, and/or innervating, receptors that are rapidly adapting, intermediate adapting, and/or slowly adapting. Electrical current, signal(s), and/or stimulation may be applied directly or indirectly to peripheral nerve(s) and the nearby and/or surrounding vicinity, which may include a predetermined distance or a predetermined range of distances, from the nerve(s).

It is to be appreciated that the methods, devices, and systems described in this invention may include the instruction, instructing, and/or providing instructions either verbally and/or in other forms, formats, and/or styles including written, printed, electronic (e.g., in instructions for use) or otherwise for the treatment of pain and/or the deployment of devices, systems, and/or components of the device or systems. As a non-limiting example, the invention may include instructing or providing instructions to use methods, devices, and/or systems to achieve the desired objective, which includes treatment of disorders and symptoms such as pain.

Control of a stimulator and/or stimulation parameters according to the present invention may be provided by one or more external controllers. In the case of an external stimulator, the controller may be integrated with the external stimulator. In the case of an implanted stimulator, an implanted pulse generator external controller (i.e., clinical programmer) may be a remote unit that uses RF (Radio Frequency) wireless telemetry communications (rather than an inductively coupled telemetry) to control the implanted pulse generator. The external or implantable pulse generator may use passive charge recovery to generate the stimulation waveform, regulated voltage (e.g., 10 mV to 20 V), and/or regulated current (e.g., about 10 µA to about 50 mA). Passive charge recovery is one method of generating a biphasic, charge-balanced pulse as desired for tissue stimulation without severe side effects due to a DC component of the current.

Figure 8A:
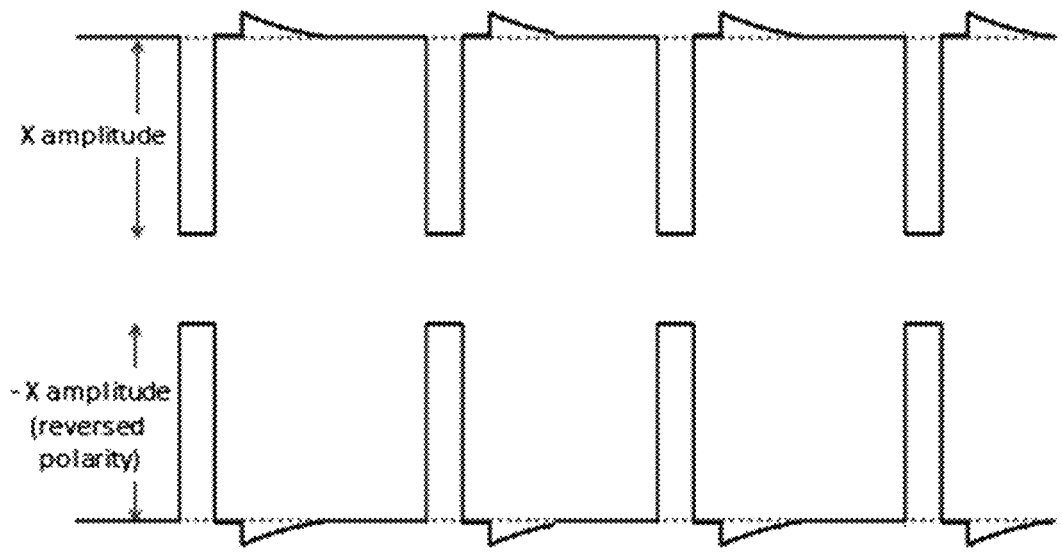
FIG. 8A through 8K are descriptive narratives and schematic examples of subthreshold electrical current signals according to certain aspects of the invention. All printed matter in these figures are incorporated within this specification.
Figure 8B:
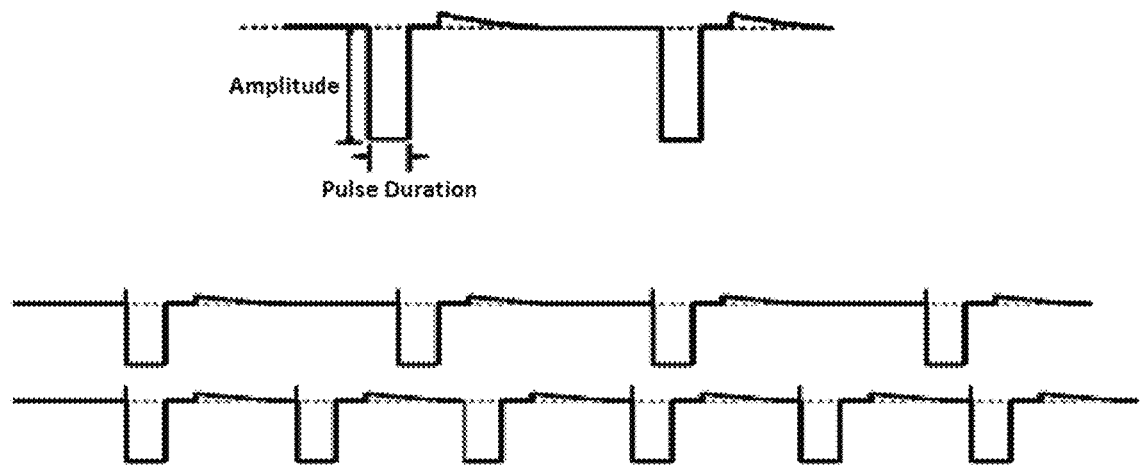
Figure 8C:
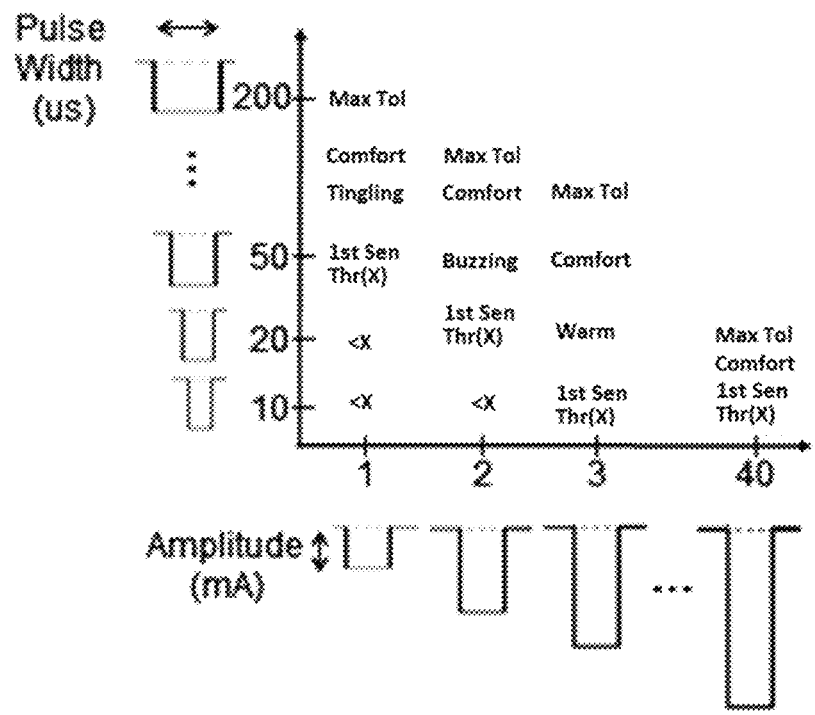

FIG. 8A illustrates an exemplary reversing polarity parameters. FIG. 8B shows an exemplary stimulus parameters. An intensity may represent a stimulus strength. In this Figure, an amplitude (pulse height) may be measured in current (e.g., mA) or voltage. Also, a pulse duration (pulse width) may be a measured in time (e.g., micro-seconds (µs)). A frequency may represent a number of pulses per second and may be measured in pulses per second (PPS) or Herz (Hz). FIG. 8C illustrates an exemplary sensation response to parameters.

Figure 8D:
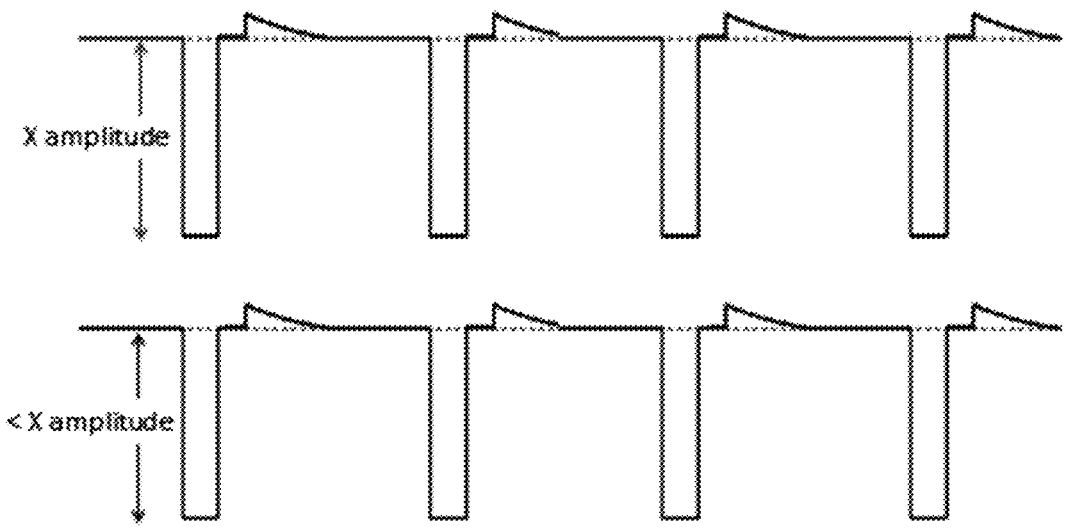
Figure 8E:
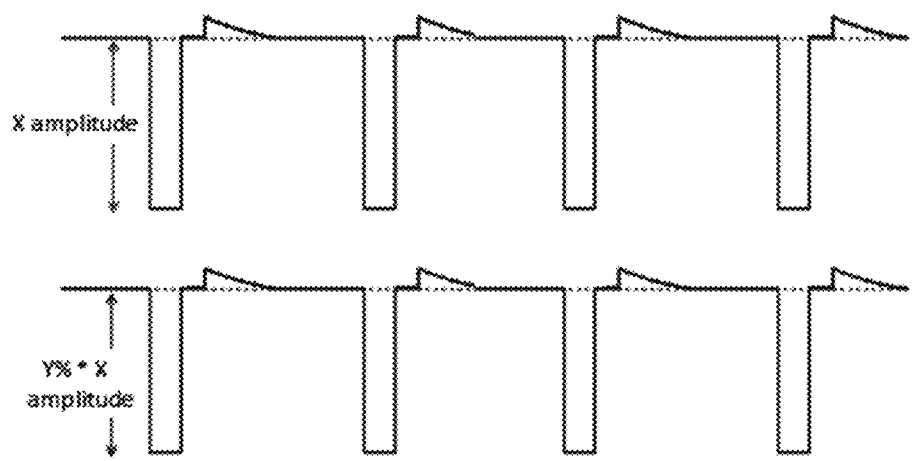
Figure 8F:
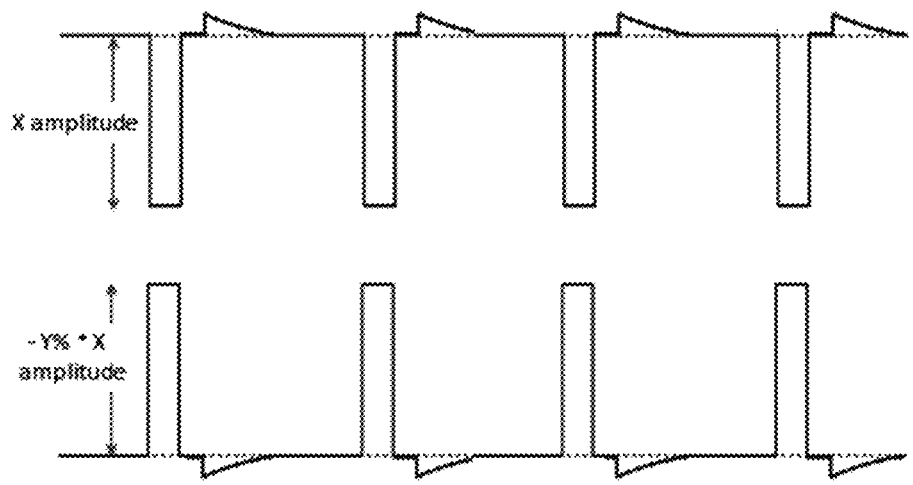

FIG. 8D and 8E illustrate some exemplary stimulus parameters. In FIG. 8F, a stimulus may reverse polarity and decrease magnitude of an amplitude (intensity). It is noted that the phases can be of any shape. It is also noted that additional phases can be used. Biphasic (2 phases) are shown, but 3 or more phases can also be used. A single phase can also be used. It is further noted that it may be desirable to recover a minimum amount of charge and the phases can be balanced or unbalanced.

Figure 8G:
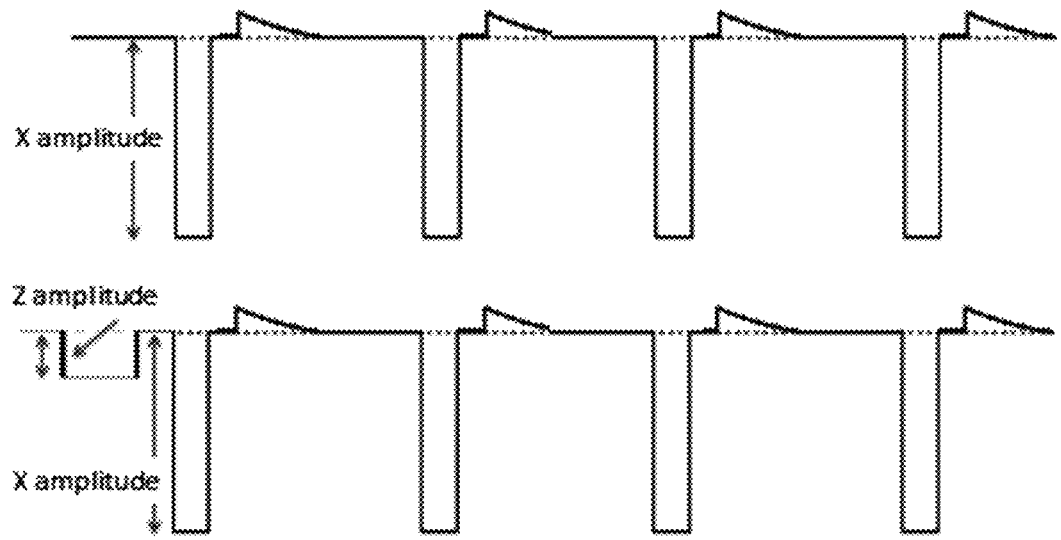

In FIG. 8G, precede the cathodic phase of the pulse with another cathodic pulse of lesser intensity (e.g., lesser amplitude and/or pulse duration). Preceding the phase of the pulse that would normally activate the nerve with a pulse (pre-pulse) with the same polarity reduces the ability of the nerve to generate an action potential while enabling the same or greater amount of current or charge to be delivered with that polarity by closing voltage gated ion channels and increasing the voltage require to excite the nerve and generate an action potential. The per-pulse characteristics and interval between pre-pulse and subsequent pulse(s) can be optimized.

Figure 8H:
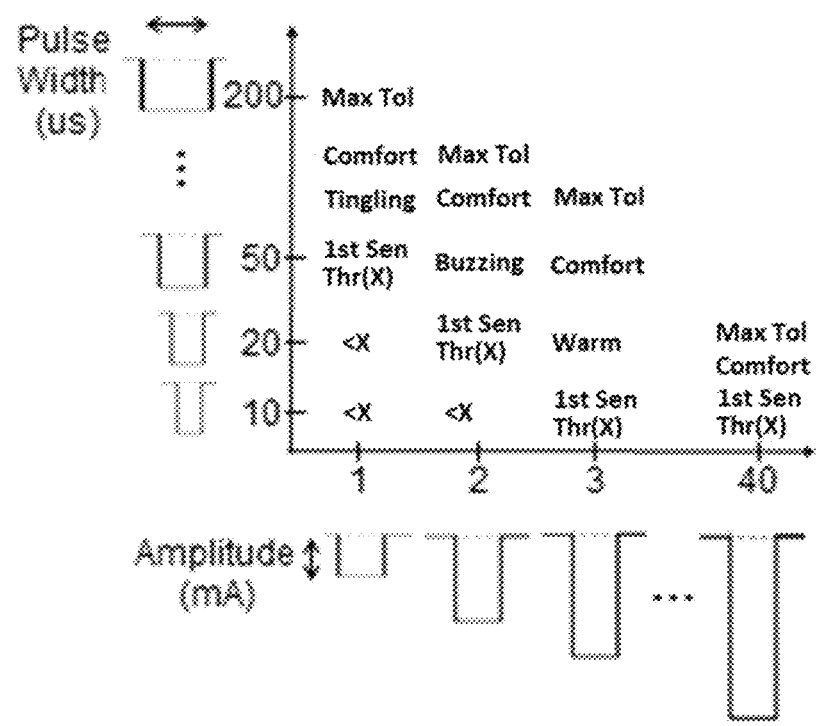
Figure 8I:
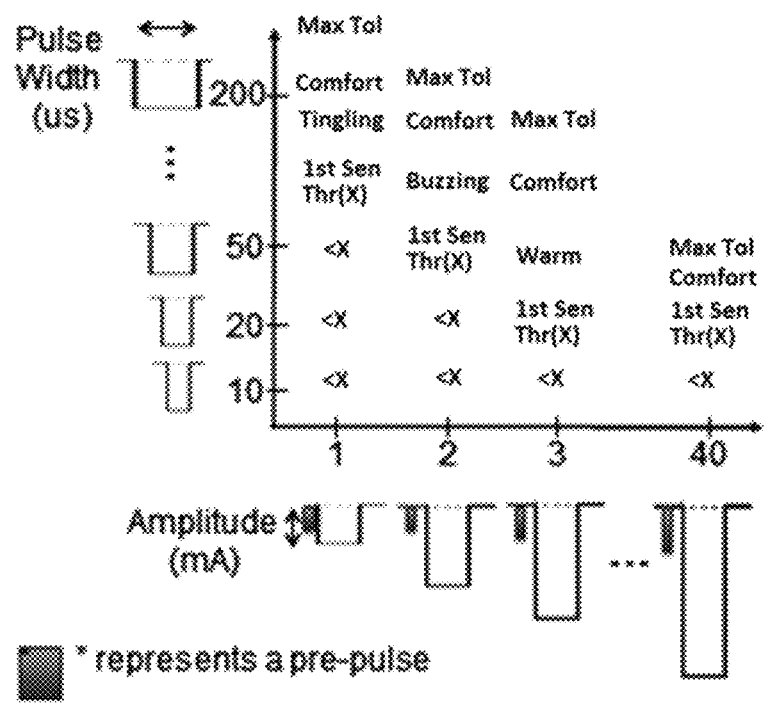
Figure 8J:
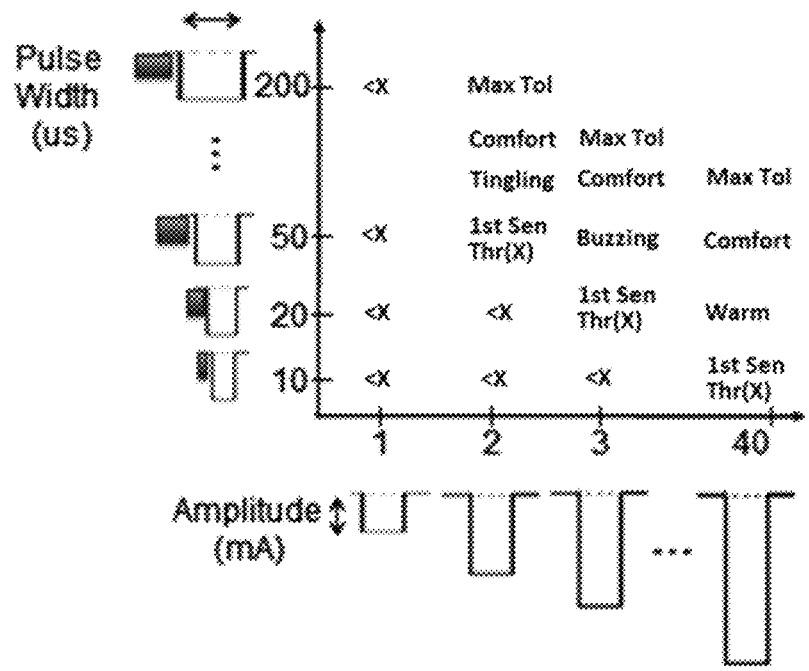
Figure 8K:
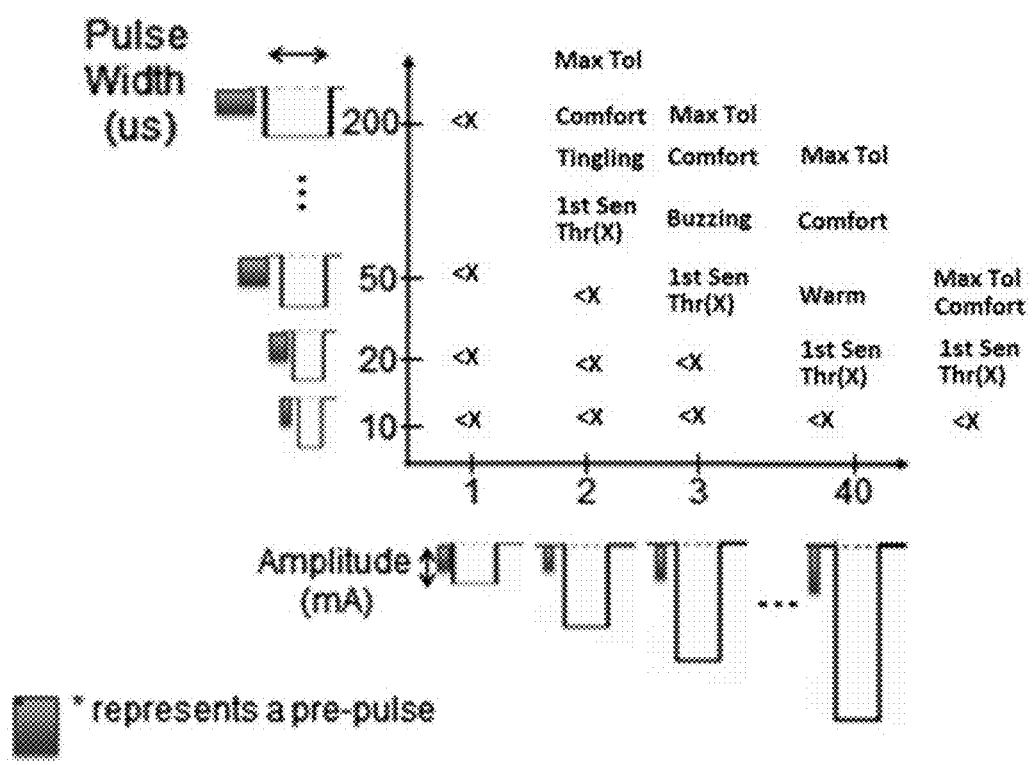

In FIGS. 8H through FIG. 8K, X may represent threshold for generating an action potential and <X indicates sub-threshold (does not generate action potential). An input such as for example, pre-pulse, may show a shift of a sensation response curve. FIG. 8H illustrates an exemplary sensation response to parameters. FIG. 8I shows that a pre-pulse can shift a response curve up. FIG. 8J illustrates that a pre-pulse can shift a response curve to the right. FIG. 8K also shows that a pre-pulse can shift a response curve up and to the right.

The neurostimulation pulse may by monophasic, biphasic, and/or multi-phasic. In the case of the biphasic or multi-phasic pulse, the pulse may be symmetrical or asymmetrical. Its shape may be rectangular or exponential or a combination of rectangular and exponential waveforms. The pulse width of each phase may range between e.g., about 0.1 µsec. to about 1.0 sec., as non-limiting examples. The preferred neurostimulation waveform is cathodic stimulation (though anodic may work), biphasic, and asymmetrical.

Pulses may be applied in continuous or intermittent trains (i.e., the stimulus frequency changes as a function of time). In the case of intermittent pulses, the on/off duty cycle of pulses may be symmetrical or asymmetrical, and the duty cycle may be regular and repeatable from one intermittent burst to the next or the duty cycle of each set of bursts may vary in a random (or pseudo random) fashion. Varying the stimulus frequency and/or duty cycle may assist in warding off habituation because of the stimulus modulation.

The stimulating frequency may range from e.g., about 1 Hz to about 300 Hz, or even as high as about 20 kHz to obtain a stochastic response, and the frequency of stimulation may be constant or varying. In the case of applying stimulation with varying frequencies, the frequencies may vary in a consistent and repeatable pattern or in a random (or pseudo random) fashion or a combination of repeatable and random patterns.

In a representative embodiment, the stimulator is set to an intensity (e.g. 1-2 mA (or 0.1-40 mA, or 0.01-200 mA), 100-300 us (or 40-1000 us, or 1-10,000 us)) sufficient to produce pain relief using an electrode that is spaced at some distance (e.g. 1 mm or more or less) away from the targeted structure. Additionally or alternatively, an electrode may be placed in direct contact with a target neural structure.

If the lead is too far away from the targeted structure, then stimulation may be unable to evoke the desired response, and if the lead is too close to the targeted nerve, then stimulation may be unable to evoke the desired response(s). In some cases, it may difficult to locate the optimal lead placement (or distance from the targeted structure) and/or it may be desirable to increase the range stimulus intensities that evoke the desired response(s) without evoking the undesired response(s) so alternative stimulus waveforms and/or combinations of leads and/or electrode contacts may be used. A non-limiting example of alternative stimulus waveforms may include the use of a pre-pulse to increase and/or decrease the effect.

As a non-limiting example, the invention provides an electrical stimulation device having at least one lead adapted for insertion within tissue of an animal body and a pulse generator operatively coupled with the at least one lead, wherein the pulse generator is configured to stimulate at least one nerve or associated structure and/or deliver electrical current or an electrical signal to a part of the peripheral nervous system to relieve or reduce pain.

The invention further provides a kit for treatment of pain having a needle insertable into an animal body tissue, at least one electrode lead operatively inserted into the needle, wherein the needle and at least one percutaneous lead are inserted into an insertion point of the animal body, whereby the needle is removable from the animal body tissue and the at least one percutaneous electrode lead is retained within the animal body, and a pulse generator operatively coupled with the at least one electrode lead, wherein the pulse generator is configured to stimulate at least one nerve.

The electrode lead can comprise, e.g., a fine wire lead and/or electrode, cylindrical lead and/or electrode, percutaneous lead and/or electrode, paddle lead and/or electrode, intramuscular lead and/or electrode, or general-purpose lead and/or electrode, inserted via a needle introducer or surgically implanted in proximity of a targeted neural structure. Once proper placement is confirmed, the needle introducer may be withdrawn, leaving the electrode(s) and/or lead(s) in place. Stimulation may also be applied through a penetrating electrode, such as an electrode array comprised of any number (i.e., one or more) of needle-like electrodes that are inserted into the target site. In both cases, the lead may placed using a needle-like introducer, allowing the lead/electrode placement to be minimally invasive.

In a representative embodiment, the lead comprises a thin, flexible component made of a metal and/or polymer material.

The lead can comprise, e.g., one or more coiled metal wires with in an open or flexible elastomer core. The wire can be insulated, e.g., with a biocompatible polymer film, such as polyfluorocarbon, polyimide, or parylene. The lead is desirably coated with a textured, bacteriostatic material, which helps to stabilize the lead in a way that still permits easy removal at a later date and increases tolerance.

The lead may be electrically insulated everywhere except at one (monopolar), or two (bipolar), or three (tripolar) (or more locations), for example, conduction locations near its distal tip. Each of the conduction locations may be connected to one or more conductors that run the length of the lead and lead extension, proving electrical continuity from the conduction location through the lead to an external pulse generator or stimulator or an implanted pulse generator or stimulator.

The conduction location or electrode may comprise a de-insulated area of an otherwise insulated conductor that runs the length of an entirely insulated electrode. The de-insulated conduction region of the conductor can be formed differently, e.g., it can be wound with a different pitch, or wound with a larger or smaller diameter, or molded to a different dimension. The conduction location or the electrode may comprise a separate material (e.g., metal or a conductive polymer) exposed to the body tissue to which the conductor of the wire is bonded.

The lead is desirably provided in a sterile package, and may be pre-loaded in the introducer needle. The package and/or kit can take various forms and the arrangement and contents of the package and may include instructions. The package can comprise a sterile, wrapped assembly. The package includes an interior tray made, e.g., from die cut cardboard, plastic sheet, or thermo-formed plastic material, which hold the contents. The package also desirably includes instructions for use for using the contents of the package to carry out the lead location and placement procedures.

The lead desirably possess mechanical properties in terms of flexibility and fatigue life that provide an operating life free of mechanical and/or electrical failure, taking into account the dynamics of the surrounding tissue (i.e., stretching, bending, pushing, pulling, crushing, etc.). The material of the electrode can desirably encourage the in-growth of connective tissue along its length, so as not to reduce unwanted displacement or migration or movement and reduce risk of infection at the lead exit site through the skin yet not inhibit its withdrawal at the end of its use. It may be desirable to encourage the in-growth of connective tissue at the distal tip of the electrode, to enhance its anchoring in tissue.

One embodiment of the lead may comprise a minimally invasive coiled fine wire lead and electrode. The electrode may also include anywhere along its length one or more anchoring elements (e.g., at or near the tip of the lead or electrode or along the length of the body of the lead). In an non-limiting example, the anchoring element can take the form of a simple barb or bend. The anchoring element(s) may also include other shapes. The anchoring element is sized and configured so that, when in contact with tissue, it takes purchase in tissue, to resist dislodgement or migration of the electrode out of the correct location in the surrounding tissue. Desirably, the anchoring element is prevented from fully engaging body tissue until after the electrode has been correctly located and deployed.

An alternative embodiment of an electrode lead, may also include, at or near its distal tip or region, one or more anchoring element(s). In a non-limiting example, the anchoring element takes the form of an array of shovel-like paddles or scallops proximal to the proximal-most electrode (although a paddle or paddles could also be proximal to the distal most electrode, or could also be distal to the distal most electrode). The paddles are sized and configured so they will not damage the surrounding tissue but will encourage healthy tissue growth around the lead to increase the ability of the device to retain its proper position. The anchoring element is sized and configured so that, when in contact with tissue, it takes purchase in tissue, to resist dislodgement or migration of the electrode out of the correct location in the surrounding tissue (e.g., muscle). Desirably, the anchoring element is prevented from fully engaging body tissue until after the electrode has been deployed. The electrode is not deployed until after it has been correctly located during the implantation (lead placement and/or insertion) process, as previously described. In addition, the lead and/or introducer may include one or more markings to aid the physician in its proper placement. The markings may be visible with and/or without imaging equipment, such as ultrasound and/or fluoroscopy.

Alternatively, or in combination, stimulation may be applied through any type of nerve cuff (spiral, helical, cylindrical, book, flat interface nerve electrode (FINE), slowly closing FINE, etc.), paddle (or paddle-style) electrode lead, cylindrical electrode lead, and/or other lead that is surgically or percutaneously placed in tissue near, at, in and/or remote from the target site.

The lead may exit (e.g., percutaneously) through the skin and connect with one or more external stimulators (e.g., such that the invention is used as a percutaneous peripheral nerve stimulator or percutaneous peripheral nerve stimulation system), or the lead(s) may be routed (e.g., below the skin, subcutaneously, through any tissue, including but not limited to muscle tissue, adipose (or fat) tissue, connective tissue, and/or any other tissue that is subcutaneous) to one or more implanted pulse generators or receivers. Alternatively, the lead(s) may be connected as needed to internal and external coils for RF (Radio Frequency) wireless telemetry communications or an inductively coupled telemetry to control the implanted pulse generator. Alternatively, the lead(s) and/or electrode(s) may not need to be tunneled (e.g., in the case that they do not need to be connected to a power source, pulse generator, receiver, and/or other circuitry because the power source, pulse generator, receiver, and/or other circuitry are integrated or otherwise connected, contained, and/or built in whole or in part into the lead(s) and/or the electrode(s). Non-limiting examples could include a leadless stimulator and/or a lead that contains both electrode(s) and circuitry, a receiver, and/or a power source. In the example of a lead connected to an implanted pulse generator, the implanted pulse generator or receiver may be located some distance (remote) from the electrode, or an implanted pulse generator may be integrated with an electrode(s) (not shown), eliminating the need to route the lead subcutaneously to the implanted pulse generator. It should be appreciated that when the electrode(s) is placed remote to the nerve or neural structure(s), the pulse generator, receiver, and/or other circuitry may or may not be located remote to the electrode(s) and also remote to the nerve or neural structure(s).

The introducer may be insulated along the length of the shaft, except for those areas that correspond with the exposed conduction surfaces of the electrode housed inside the introducer. These surfaces on the outside of the introducer may be electrically isolated from each other (or connected to each other) and from the shaft of the introducer. These surfaces may be electrically connected to a connector at the end of the introducer body. This allows connection to an external stimulator during the implantation process. Applying stimulating current through the outside surfaces of the introducer provides a close approximation to the response that the electrode will provide when it is deployed at the current location of the introducer.

The introducer may be sized and configured to be bent by hand prior to its insertion through the skin. This will allow the physician to place lead in a location that is not in an unobstructed straight line with the insertion site. The construction and materials of the introducer allow bending without interfering with the deployment of the lead and withdrawal of the introducer, leaving the lead in the tissue.

Those skilled in the art will recognize that, for simplicity and clarity, the full structure and operation of all devices and processes suitable for use with the present invention is not being depicted or described herein. Instead, only so much of an implantable pulse generator and supporting hardware as is unique to the present invention or necessary for an understanding of the present invention is depicted and described. The remainder of the construction and operation of the IPGs described herein may conform to any of the various current implementations and practices known in the art.

Although the present embodiments have been illustrated in the accompanying drawings and described in the foregoing detailed description, it is to be understood that the invention is not to be limited to just the embodiments disclosed, and numerous rearrangements, modifications and substitutions are also contemplated. The exemplary embodiment has been described with reference to the preferred embodiments, but further modifications and alterations encompass the preceding detailed description. These modifications and alterations also fall within the scope of the appended claims or the equivalents thereof.

The invention claimed is:

1. A method of treating pain comprising:
   deploying an open-coiled lead comprising an electrode, wherein the electrode is deployed outside of a central nervous system;
   delivering electric current through the electrode to one peripheral nerve tissue;
   altering, through the electric current, transmission and production of action potentials in the one peripheral nerve tissue, which is selected from a nerve cell body, dendrites, axons, axon hillocks, or other nerve fibers, wherein the altering occurs without directly stimulating an action potential in the peripheral nerve tissue; and
   changing probability of action potentials occurring as a result of the electric current;
   changing excitability of at least one nerve as a result of the electric current; and
   changing conduction velocity, shape, or interpulse interval of action potentials as a result of the electric current and wherein the electrical current does not block or interrupt efferent signals and motor nerve signals.

2. The method of claim 1, wherein the electrical current does not cause paresthesias.

3. The method of claim 1 wherein the electrical current alters action potentials in neural targets via activation, inactivation, excitation, or suppression of non-neural tissue.

4. The method of claim 3 wherein the non-neural tissue is a glial cell.

5. The method of claim 1 wherein the electrical current is delivered through the electrode located 1.0 mm or more away from the nerve tissue.

6. The method of claim 1, wherein the electric current causes changes to a frequency of action potentials.

7. The method of claim 1, wherein the electric current causes changes to form, features, period, rate, coefficient of variation, or duration of action potentials.

8. The method of claim 7, wherein the electric current causes changes to timing, spacing, or pattern of action potentials or trains of action potentials.

9. The method of claim 1, wherein the electric current causes changes to a frequency of action potentials and changes to form, features, period, rate, coefficient of variation, or duration of action potentials.

10. A method of treating pain comprising:
    deploying an open-coiled lead into a tissue, the lead comprising an electrode positioned outside of a central nervous system;
    altering transmission of action potentials in one peripheral nerve tissue selected from a nerve cell body (or soma), dendrites, axons, axon hillocks, or other nerve fibers
    changing a probability of action potentials occurring through application of electrical stimulation via the electrode;
    changing excitability of at least one nerve of said peripheral nerve tissue through the application of the electrical stimulation via the electrode; and
    changing conduction velocity, shape, or interpulse interval of action potentials through the application of the electrical stimulation via the electrode wherein the electrical current does not block or interrupt efferent signals and motor nerve signals.

11. A method of treating pain comprising:
    deploying an open-coiled lead into a tissue, the lead comprising an electrode positioned outside of a central nervous system;
    delivering electric current to one peripheral nerve via the electrode;
    altering transmission and production of action potentials in the one peripheral nerve tissue selected from a nerve cell body, dendrites, axons, axon hillocks, or other nerve fibers without directly stimulating an action potential in the peripheral nerve tissue;
    changing probability action potentials occurring caused by the electric current;
    changing excitability of at least one nerve caused by the electric current; and
    changing conduction velocity, shape, interpulse interval of action potentials caused by the electric current and wherein the electrical current does not block or interrupt efferent signals and motor nerve signals.

* * * * *